US008008460B2

(12) United States Patent
Wolff et al.

(10) Patent No.: US 8,008,460 B2
(45) Date of Patent: *Aug. 30, 2011

(54) POLYNUCLEOTIDE FRAGMENTS OF AN INFECTIOUS HUMAN ENDOGENOUS RETROVIRUS

(75) Inventors: Klaus Wolff, Vienna (AT); Hubert Pehamberger, Vienna (AT); Andreas Grassauer, Vienna (AT); Thomas Muster, Vienna (AT)

(73) Assignee: Avir Green Hills Biotechnology Research Development Trade AG, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 12/261,374

(22) Filed: Oct. 30, 2008

(65) Prior Publication Data

US 2009/0180975 A1    Jul. 16, 2009

Related U.S. Application Data

(63) Continuation of application No. 10/490,920, filed as application No. PCT/EP02/10899 on Sep. 27, 2002, now Pat. No. 7,510,862.

(30) Foreign Application Priority Data

Sep. 27, 2001 (AT) ................ A 1539/2001

(51) Int. Cl.
*C07H 21/02* (2006.01)
*C07H 21/04* (2006.01)
*C12N 15/00* (2006.01)

(52) U.S. Cl. ............... 536/23.1; 536/24.3; 435/320.1

(58) Field of Classification Search ........... 536/23.1, 536/24.3; 435/320.1

See application file for complete search history.

(56) References Cited

U.S. PATENT DOCUMENTS

| 6,395,549 B1* | 5/2002 | Tuan et al. ............... 435/455 |
| 6,396,549 B1 | 5/2002 | Weber ...................... 348/734 |
| 6,500,869 B1 | 12/2002 | Driller et al. ............ 514/931 |
| 7,256,274 B2 | 8/2007 | Noteborn et al. ........ 536/23.1 |

FOREIGN PATENT DOCUMENTS

| DE | 19811692 | 9/1999 |
| JP | 9252780 | 9/1997 |
| WO | WO 98/24454 | 6/1998 |
| WO | WO 99/67395 | 12/1999 |
| WO | WO 00/06598 | 2/2000 |
| WO | WO 00/20460 | 4/2000 |
| WO | WO 00/53789 | 9/2000 |
| WO | WO 01/62937 | 8/2001 |
| WO | WO 01/70941 | 9/2001 |
| WO | PCT/EP02/10899 | * 4/2003 |

OTHER PUBLICATIONS

Balda et al., "Oncornavirus-like particles in human skin cancers," *Proc. Natl. Acad. Sci.*, USA, 72(9):3697-3700, 1975.
Barbulescu et al., "A HERV-K provirus in chimpanzees, bonobos and gorillas, but not humans," *Current Biology*, 11(10):779-783, 2001.
Barbulescu et al., "Many human endogenous retrovirus K (HERV-K) proviruses are unique to humans," Current Biology, 9(4):861-868, 1999.
Bartlett et al., "Overview of the effectiveness of triple combination therapy in antiretroviral-naïve HIV-1 infectedadults,"*AIDS*,15(11):1369-1377, 2001.
Birkmayer et al., "Oncorna-viral information in human melanoma," *Europe. J. Cancer*, 10:419-422, 1974.
Birkmayer et al., "Virus-like particles in metastases of human malignant melnoma," *Die Naturwissenschaften*, 59(8):36-370, 1972.
Burke, "Clearing the way for ribozymes," *Nature Biotechnology*, 15:414-415, 1997.
Ferko et al., "Hyperattenuated recombinant influenza A virus nonstructural-protein-encoding vectors induce human immunodeficiency virus type 1 nef-specific systemic and mucosal immune responses in mice," *J. Virol.*, 75(19):8899-8908, 2001.
GenBank Accession No. AF164614.
Komurian-Pradel et al., "Rapid communication molecular cloning anc characterization of MSRV-related sequences associated with retrovirus-like particles," *Virology*, 260(1):1-9, 1999.
Kuwabara et al., "Formation of a catalytically active dimer by trna val-driven short ribozymes," *Nature Biotechnology*, 16:961-965, 1998.
Löwer et al., "Identification of human endogenous retroviruses with complex mRNA espression and particle formation," *Proc. Natl. Acad. Sci.*, USA, 90:4480-4484, 1993.
Löwer et al., "The viruses in all of us: characteristics and biological significance of human endogenous retrovirus sequences,"*Proc. Natl. Acad. Sci.*, USA, 93(11):5177-5184, 1996.
Marimoutou et al., "Prognostic factors of combined viral load and CD4+ cell count responses under triple antiretroviral therapy, Aquitaine cohort," *J. Acquir. Immune Defic Syndr.*, 27(2):161-167, 1996-1998.
Muster et al., "An endogenous retrovirus derived from human melanoma cells," *Cancer Res.*, 63(24):8735-41, 2003.
Muster et al., "Detection of viral sequences and virus-like particles in human melanoma," J. Invest. Dermatology, 114(4):860, 2000.
Office Communication, dated Oct. 10, 2006.
Office Communication, dated Sep. 25, 2007.
Office Communication, dated May 29, 2008.
Pooga et al., "Cell penetrating DNA constructs regulate alanin receptor levels and modify transmission in vivo," *Nature Biotechnology*, 16:857-861, 1998.
Reus et al., "Genomic organization of the human endogenous retrovirus HERV-K(HML-2.HOM)(ERVK6) on chromosome 7," *Genomics*, 72(3):314-320, 2001.
Reus et al., "HERV-K(OLD): ancestor sequences of the human endogenous retrovirus family HERV-K(HML-2)," *J. Virol.*, 75(19) 8917-8926, 2001.
Turner et al., "Insertional polymorphisms of full-length endogenous retroviruses in humans," *Current Biology*, 11(19):1531-1535, 2001.

* cited by examiner

*Primary Examiner* — Wu-Cheng Winston Shen
(74) *Attorney, Agent, or Firm* — Fulbright & Jaworski LLP

(57) ABSTRACT

Nucleotide sequences and fragments which code for a human endogenous retrovirus which is infectious. "Fragments" according to the present invention relate also to specific fragments of the sequences inserted into the vector pCR4-Topo and deposited as MERV-env, MERV-gag, MERV-prt and MERV-pol as mentioned above. Additionally, methods of using such sequences, polypeptides encoded by such sequences, antibodies directs against such sequences, and methods and compositions relating to the same are all contemplated.

13 Claims, 11 Drawing Sheets

A

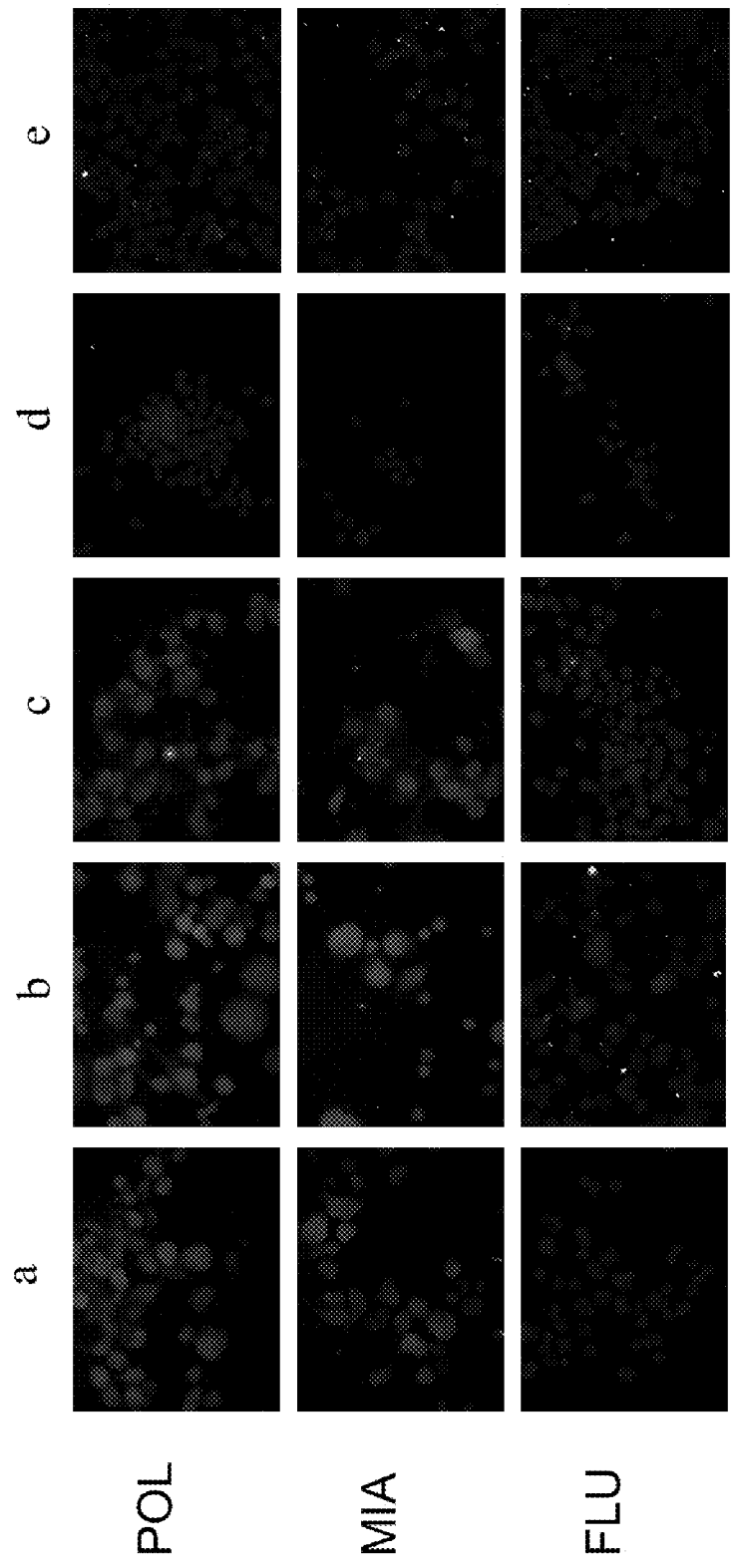

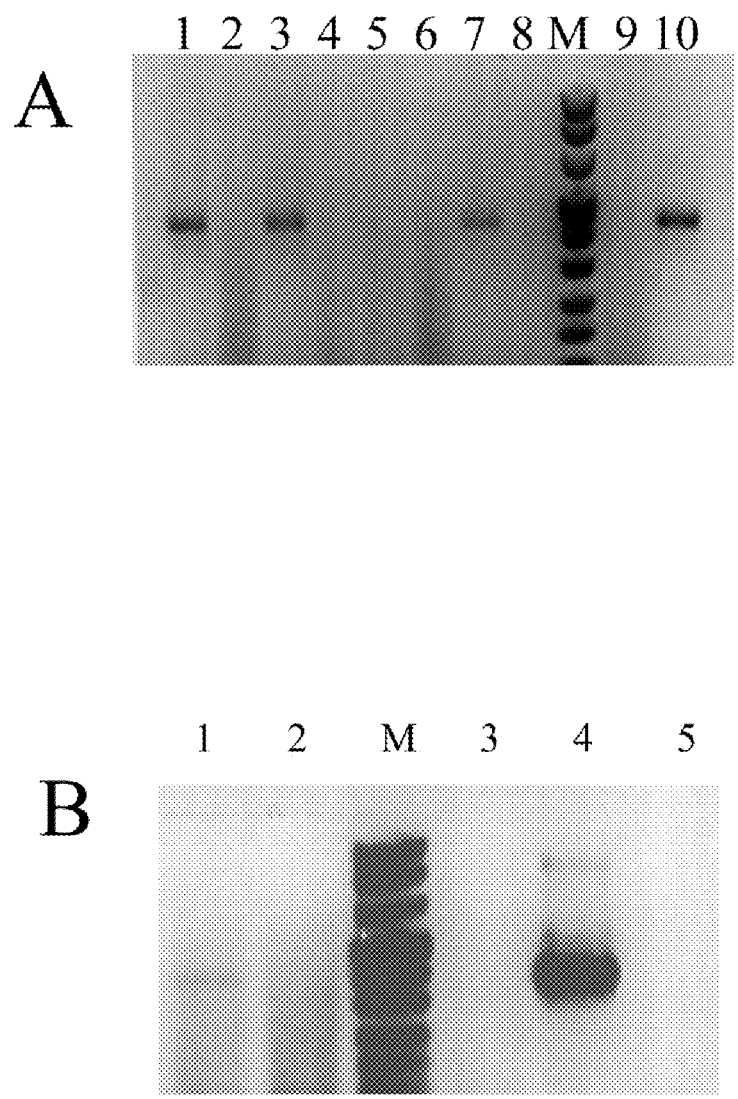
FIG. 7A-B

FIG. 8B

MERV gag

SEQ ID NO:50 | ...TTAAACGAATTCGCCCTT | GCTAGGGTGATAATGGGGCAAACT | AAAAGTAAAATTAAAAGTAAATATGCCTCTTATCTC...
Vektor pCR4-TOPO | Primer | gag-Sequenz ...AAGCCAGTTACCACAATACAACAATTGTCCCCCACCA | CAAGCGGCAGTGCAGCAGTAC | AAGGGCGAATCGCGGCCGCT...
gag-Sequenz | Primer | Vektor pCR4-TOPO

MERV prot

SEQ ID NO:51 | ...TTAAACGAATTCGCCCTT | CAAGCGGCAGTGCAGCAGTAG | ATTTATGTACTATACAAGCAGTCTCTCTGCTTCCAGGGG...
Vektor pCR4-TOPO | Primer | prot-Sequenz ...TTTTTACCATCCCTCTGGCGGAGCAGGATTGC | GAAAAATTTGCCTTTACTATAC...GC | AAGGGCGAATCGCGGCCGCT...
prot-Sequenz | Primer | Vektor pCR4-TOPO

MERV pol

SEQ ID NO:52 | ...TTAAACGAATTCGCCCTT | GAAAAATTTGCCTTTACTATACCAGC | CATAAATAATAAAGAACCAGCCACCAGGTTTCAG...
Vektor pCR4-TOPO | Primer | pol-Sequenz ...CTTCCTGTTTGGATACCCACTAGACATTTGAAGTT | CTACAATGAACCCATCAGAGAGC | AAGGGCGAATCGCGGCCGCT...
pol-Sequenz | Primer | Vektor pCR4-TOPO

MERV env

SEQ ID NO:53 | ...TTAAACGAATTCGCCCTT | CTACATGAACCCATCAGAGATGCAAAGAAAAGC | ACCTCCGCGGAGACGGAGNACACCGCA...
Vektor pCR4-TOPO | Primer | env-Sequenz ...CAAGAGAGATCAGATTGTCACTGTGTCTGTGTAC | AAAGAAGTAGACATAGGAGACTCC | AAGGGCGAATCGCGGCCGCT...
env-Sequenz | Primer | Vektor pCR4-TOPO

POLYNUCLEOTIDE FRAGMENTS OF AN INFECTIOUS HUMAN ENDOGENOUS RETROVIRUS

CROSS REFERENCE TO RELATED APPLICATIONS

This application is a continuation of U.S. application Ser. No. 10/490,920 filed 26 Mar. 2004 now U.S. Pat. No. 7,510,862, which is a national phase application under 35 U.S.C. §371 of International Application No. PCT/EP02/10899 filed 27 Sep. 2002, which claims priority to Austrian Application No. A 1539/2001 filed 27 Sep. 2001, the contents of which are incorporated herein by reference in their entirety.

BACKGROUND OF THE INVENTION

1. Field of the Invention

The present invention relates to human endogenous retroviruses, fragments thereof, a biologically functional vector comprising sequences of said retrovirus.

2. Description of Related Art

Endogenous retroviruses (ERVs) are integral parts in the genomes of many, if not of all, species. ERVs most probably, resulted from infection of germ line cells with exogenous retroviruses and subsequent fixation of their genetic information in the host genome.

Many types of human endogenous retroviruses (HERVs) have been characterized previously, and they have been classified into different groups, or families, partly on the basis of their sequence identity and partly according to the similarity of their primer binding sites (PBSs) to host tRNAs. Thus, members of the HERV.H family contain a PBS with a sequence similar to a region of tRNA$^{His}$, whereas the HERV.E family is primed by tRNA$^{Glu}$. Despite the large amount of data available, the classification of the many different HERV families within an overall phylogenetic framework has been hampered for several reasons: (i) some highly divergent retroviruses are primed by the same type of tRNA; (ii) many HERV families have not been fully characterized, and the sequence information that has been reported is often derived from different genomic regions, making interfamily comparisons problematic; and (iii) the relative lack of sequence information on other host taxa has made it difficult to distinguish between genuinely monophyletic HERV families and polyphyletic families that appear monophyletic only because similar viruses in other hosts have not yet been described. A pathogenic potential of nondefective endogenous retroviruses has so far only been demonstrated in mice, in which they may induce tumors and immunological disorders. In human DNA, endogenous retrovirus sequences (HERVs) are well known genetic elements. They all seem to be defective due to multiple termination codons, deletions, or the lack of a 5' long terminal repeat (LTR). Replication competent human endogenous retrovirus genomes have not yet been isolated.

Extensive studies on animal melanomas (especially that of the hamster), which serve as model for human malignant melanoma have shown the occurrence of virus particles in the tumors. A high molecular weight (70S) RNA species as well as an RNA-directed DNA polymerase, two diagnostic features for oncorna (oncogenic RNA) viruses have been associated with these particles. Cell-free transmission experiments end to the conclusion that hamster melanomas are caused by an RNA virus.

Based on these findings the working hypothesis was proposed that human melanoma may also have a viral etiology. In experiments the occurrence of virus-like particles as well as reverse transcriptase activity in metastases of human melanoma was reported in the early 70s. (Birkmayer et al., *Europ. J. Cancer* 10 (1974) 419-422).

These virus-like particles are spherical or slightly ovoid and have a diameter of 90-120 nm. They have an electron-dense nucleoid measuring 50-70 nm across and are bounded by a triple-layered, 100 Å thick membrane. Sometimes fine projections extend radially from the nucleoid towards the membrane, and in this case the particles resemble those found in hamster melanoma. Their number is rather small in comparison to that found in hamster melanoma. So far, they have been seen only in the cytoplasm and no infectivity has been observed for these particles (Birkmayer et al., *Die Naturwissenschaften* 59 (8) (1972), 369-370).

Also Balda et al. (*Proc. Nat. Acad. Sci, USA* 72 (9) (1975, 3697-3700) described a high molecular weight RNA encapsulated with an RNA extracted DNA polymerase in particles possessing the identity characteristic of the RNA tumor viruses which was detected in human malignant melanomas. However, also here no infectious particles were observed.

Only many years later the expression of a family of human endogenous retrovirus sequences (HERV-K) in GH cells, a teratocarcinoma cell line producing the human teratocarcinoma-derived retrovirus (HTDV) particles was described (Löwer et al., Proc. Natl. Acad. Sci. USA 90 (1993): 4480-4484). Detailed electron microscopic surveys have revealed the existence of retrovirus-like particles in human placentas and teratocarcinoma cell lines. However, these found HERV-K/HTDV particles were also not infectious: They possess a distinct morphology: (i) they lack the electron lucent space normally seen between viral envelope and core, (ii) they seem to be predominantly arrested in budding stages, and (iii) collapsed cores, a consequence of a final proteolytic step in virus maturation, have never been observed. As long as the gag precursor remains uncleaved, resulting particles are not likely to be infectious.

A further HERV-K provirus was shown to be present in gorilla and chimpanzee genomes but not in the human genome (Barbulescu et al., *Current Biology* 11 (10) (2001), 779-783).

Therefore, human endogenous retroviruses have shown to be expressed, however, these virus particles found up to date were all non-infectious virus particles. Some endogenous retrovirus-like particles were found to be expressed in melanoma cells. However, the only infectious endogenous retroviruses found were some animal endogenous retroviruses, e.g. MelARV, a retrovirus capable of infecting cultured murine melanocytes which have also been shown to induce in some instances malignant transformation.

In the article by Reus et al. (Journal of Virology, October 2001, 8917-8926) it is stated that the average age of HERV-K proviruses is ca. 28 million years. It is described that at that time the HERV-Ks probably used to be infectious.

The WO 01/62937 A1 relates to retrovirus sequences and psoriasis.

In the WO 00/53789 A1 various retroviral expression vectors are listed.

The WO 00/20460 A1 relates to the detection of a HERV-K10 gag-sequence which is brought into relationship with the cancer seminoma, whereby the HERV-K10 gag-sequence is used as tumor marker as well as for therapeutic methods.

In the WO 00/06598 A1 a HERV-AVL3-B sequence fragment is brought in connection with methods for the treatment for malign melanomas.

The WO 99/67395 A1 relates to a 600 bp sequence of an env-gene of a virus family HERV-7q and relates to the use for or in connection with multiple sclerosis, and autoimmune diseases, respectively.

In the WO 98/24454 A1 the use of a retroviral ribozyme sequence described HERV-PTN for the inhibition of tumor growth is described.

The JP 9252780 A relates to a method, in which a retrovirus polypeptide of the type HERV-E as a surrogate marker for cancer and other illnesses is detected.

The WO 01/70941 A2 relates to a retroviral sequence with high homology to the family HERV-H, whereby this sequence is brought into connection with multiple sclerosis.

The DE 198 11 692 A1 relates to a preparation for the protection against sun rays which is effective against herpes simplex viruses, whereby the preparation comprises organic and anorganic light filters.

SUMMARY OF THE INVENTION

The object of the present invention is therefore to provide at least a fragment of a nucleotide sequence which codes for a further human endogenous retrovirus which is infectious.

The object of the present invention is solved by a polynucleotide molecule being a fragment of a nucleotide sequence of an infectious human endogenous retrovirus which polynucleotide molecule comprises a sequence selected from the group consisting of
  (a) a sequence with at least 98%, preferably 99%, still preferred 99.5%, identity to a sequence according to SEQ ID No 1,
  (b) a sequence which hybridizes under stringent conditions with a nucleotide sequence according to said SEQ ID No 1,
  (c) a sequence which differs from said sequences (a) or (b) due to degeneration of the genetic code and
  (d) a sequence comprising sequences inserted into vectors pCR4-Topo and deposited as "MERV-env", "MERV-gag", "MERV-prt" and "MERV-pol" at the DSMZ on 26 Sep. 2001 or fragments thereof.

It has been surprisingly found that a polynucleotide molecule as mentioned above codes for (parts of) an infectious human endogenous retrovirus. With the present invention it can be shown for the first time that not only infectious animal endogenous retroviruses exist but also infectious human endogenous retroviruses. This is particularly surprising due to the fact that human endogenous retroviruses have been known and described for more than 30 years, however, even though many groups have been carrying out research in this field over decades, infectious human endogenous retroviruses could not be isolated or detected so far.

The polynucleotide molecule according to the present invention is preferably an isolated and a purified DNA or RNA molecule.

"Infectious" in the scope of the present application relates especially to retrovirus particles which are able to bind to the receptor of a cell over the env protein and enter into the cell and carry out a reverse transcription in order to produce a cDNA which can integrate into the host cell DNA. The differences between the life cycles of different retro elements and between infectious and non-infectious retroviruses is described in the article by Löwer et al. (*Proc. Natl. Acad. Sci* 93 (1996), 5177-5184), which is incorporated herein by reference.

Preferably, "infectious" human endogenous retroviruses according to the present invention are able to infect bovine MDBK cells and to integrate into these cells' genome.

The sequence according to SEQ ID NO 1 comprises a region which must be present in the polynucleotide molecule in order to code for an infectious human endogenous retrovirus (HERV). However, at both ends the polynucleotide molecule according to the present invention can comprise further herein not specifically described sequence regions, in particular LTR regions common to such viruses. With the present polynucleotide molecule any here not defined sequence regions can be identified by e.g. amplifying these sequences with the help of optimally designed gene specific primers which will for example bind to the above defined sequence regions. The amplification products can then be sequenced. Such methods are well known to the person skilled in the art.

"Stringent conditions" relate to hybridization reactions under defined hybridization conditions which is a function of factors as concentration of salt or formamide in the hybridization buffer, the temperature of the hybridization and the post-hybridization wash conditions. Such conditions for Northern Blot analysis are for example hybridization at 68° C. with a MERV-specific polynucleotide molecule labeled with dioxigenin or radioactive in a standard SSC hybridization buffer containing 0.1% SDS followed by stringent washing in wash buffer at the same temperature. Stringent washing can be performed for example by two times washing with 2× SSC buffer followed by two wash steps with 0.5× SSC buffer. In the present case stringent hybridization conditions will preferably involve a temperature of 15° C. to 25° C. below the melting temperature (Tm), whereby the Tm of a hybridization product of a nucleic acid probe can be calculated using a formula based on the g+c contained in the nucleic acids and that takes chain lengths into account, such as the formula Tm=81.5 to 16.6 (log [na$^+$])+0.41 (% G+C)−600/N), wherein N=chain length (Sambrook et al. (1989), which is incorporated herein by reference). In practice an estimated Tm for an oligonucleotide probe is often confirmed and thus a person skilled in the art can calculate the Tm for any chosen probe whose nucleotide sequence is known.

Sequences which differ from a given sequence due to the degeneration of the genetic code can be defined by any person skilled in the art. This can be carried out electronically without undue burden.

In the scope of the present application the deposited vectors MERV-env, MERV-gag, MERV-prt and MERV-pol refer to plasmids deposited at the DSMZ (Deutsche Sammlung von Mikroorganismen und Zellkulturen GmbH) according to the Budapest Treaty and comprise the accession numbers DSM14540, DSM14538, DSM14536 and DSM14537.

In the scope of the present invention, when sequences inserted into the deposited vectors are concerned not only identical sequences are referred to but also sequences
  (a) with at least 98%, preferably 99%, still preferred 99.5%, identity to the sequences inserted into the deposited vectors,
  (b) which hybridize under stringent conditions with sequences inserted into the deposited vectors and
  (c) which differ from said sequences inserted into the deposited vectors due to degeneration of the genetic code.

The above polynucleotide molecule according to the present invention may further comprise a sequence which is at least 99.7%, 99.8% or 99.9% identical to SEQ ID NO 1.

Preferably, the polynucleotide molecule comprises a sequence according to SEQ ID NO 1 and is therefore identical to SEQ ID NO 1. This polynucleotide molecule has shown to code for a complete and active infectious particle of a HERV. The ORFs of SEQ ID NO 1 are preferably as follows:

| ORF | Nucleotides | genetic code |
|---|---|---|
| gag | 1-2013 | universal |
| prt | 1993-2809 | nested reading frame |
| pol | 3032-5650 | universal |
| env | 5352-7451 | universal |

Still preferred a polynucleotide molecule is provided which comprises a specific fragment of said above described polynucleotide molecule with a length of at least 15 bp, preferably at least 20 bp, still preferred at least 30 bp. The term "specific" defines any fragment which comprises a sequence different to any known HERV sequence. Therefore, any fragment with a length of at least 15 bp which comprises, for example, the in Table 1 mentioned mutations with respect to the known non-infectious HERV K (GeneBank, accession nr. 164614) will be comprised by the polynucleotide molecule according to the present invention. However, these given lengths are minimum lengths and also fragments which are longer, e.g. 100, 1000, 1500 bp, are also comprised by the term "fragment".

"Fragments" according to the present invention relate also to specific fragments of the sequences inserted into the vector pCR4-Topo and deposited as MERV-env, MERV-gag, MERV-prt and MERV-pol as mentioned above.

TABLE 1

| clone name | position in MERV | position in HERV K108 (Accession 164614) | nucleotide change (MERV/ HERV) | amino acid change (MERV/ HERV) |
|---|---|---|---|---|
| MERV gag | 416 | 1515 | C/T | Ala/Val |
| | 602 | 1701 | C/A | Arg/Lys |
| | 630 | 1729 | A/G | Pro/Pro |
| | 639 | 1738 | T/C | Ala/Ala |
| | 654 | 1753 | G/T | Pro/Pro |
| | 738 | 1837 | G/A | Pro/Pro |
| | 799 | 1898 | G/A | Glu/Lys |
| | 802 | 1901 | C/T | Leu/leu |
| | 866 | 1965 | T/C | Met/Thr |
| | 945 | 2044 | A/G | Ser/Ser |
| | 953 | 2052 | T/A | Met/Lys |
| | 972 | 2071 | A/G | Glu/Glu |
| | 1149 | 2248 | A/G | Gln/Arg |
| | 1348 | 2447 | A/G | Lys/Gly |
| | 1413 | 2512 | C/T | Ala/Ala |
| | 1642 | 2741 | G/A | Gly/Arg |
| | 1653 | 2752 | C/T | Tyr/Tyr |
| | 1668 | 2767 | C/T | Ile/Ile |
| | 1701 | 2800 | C/T | Asn/Asn |
| | 1989 | 3088 | A/G | Pro/Pro |
| MERV prot | 2068 | 3167 | T/C | Ile/Thr |
| | 2087 | 3186 | C/A | Gly/Gly |
| | 2090 | 3189 | A/C | Pro/Pro |
| | 2097 | 3196 | G/A | Glu/Lys |
| | 2100 | 3199 | A/G | Arg/Gly |
| | 2124 | 3223 | A/C | Arg/Arg |
| | 2163 | 3262 | G/A | Gly/Ser |
| | 2198 | 3297 | G/A | Gln/Gln |
| | 2238 | 3337 | G/A | Gly/Arg |
| | 2253 | 3352 | G/C | Glu/Gln |
| | 2273 | 3372 | T/C | Tyr/Tyr |
| | 2305 | 3404 | C/T | Thr/Ile |
| | 2313 | 3412 | T/C | Phe/Leu |
| | 2330 | 3429 | G/A | Pro/Pro |
| | 2461 | 3560 | G/A | Arg/Gln |
| | 2501 | 3600 | T/A | Gly/Gly |
| | 2502 | 3601 | T/C | Phe/Leu |
| | 2543 | 3642 | T/G | Thr/Thr |
| | 2554 | 3653 | G/A | Arg/His |
| | 2590 | 3689 | G/A | Arg/Gln |
| | 2654 | 3753 | A/G | Ala/Ala |

TABLE 1-continued

| clone name | position in MERV | position in HERV K108 (Accession 164614) | nucleotide change (MERV/ HERV) | amino acid change (MERV/ HERV) |
|---|---|---|---|---|
| | 2659-2661 | 3758-3760 | —/ATC | —/Ile |
| | 2677 | 3776 | T/C | Leu/Ser |
| | 2741 | 3840 | A/G | Gly/Gly |
| | 2763 | 3862 | G/A | Val/Ile |
| | 2808 | 3907 | T/A | Tyr/Asn |
| | 2815 | 3914 | T/G | Phe/Cys |
| | 2816 | 3915 | T/C | Phe/Cys |
| MERV prot | 2878 | 3977 | G/A | Arg/Gln |
| | 2938 | 4037 | G/A | Arg/Gln |
| | 2974 | 4073 | A/G | His/Arg |
| | 3052 | 4151 | C/T | Ala/Ala |
| | 3091 | 4190 | T/C | Pro/Pro |
| | 3105 | 4204 | T/C | Leu/Pro |
| | 3124 | 4223 | C/T | Leu/Asp |
| | 3178 | 4277 | G/A | Ala/Ala |
| MERV pol | 3363 | 4462 | A/G | Tyr/Cys |
| | 3664 | 4763 | A/C | Ile/Ile |
| | 3700 | 4799 | A/G | Ile/Met |
| | 4040 | 5139 | C/A | Gln/Lys |
| | 4115 | 5214 | A/T | Met/Leu |
| | 4219 | 5318 | G/A | Gly/Gly |
| | 4225 | 5324 | G/A | Lys/Lys |
| | 4255 | 5354 | T/G | Ser/Ser |
| | 4336 | 5435 | C/A | Ala/Ala |
| | 4465 | 5564 | T/A | Thr/Thr |
| | 4517 | 5616 | G/C | Glu/Gln |
| | 4771 | 5870 | G/A | Ser/Ser |
| | 4780 | 5879 | T/C | His/His |
| MERV env | 5402 | 6501 | C/T | His/His |
| | 5719 | 6818 | T/C | Ile/Thr |
| | 6456 | 7555 | G/A | Val/Ile |
| | 6458 | 7557 | C/T | Val/Ile |
| | 6464 | 7563 | A/G | Leu/Leu |
| | 6802 | 7901 | G/C | Gly/Ala |
| | 7146 | 8245 | A/G | Lys/Glu |
| | 7262 | 8361 | A/G | Thr/Thr |
| | 7340 | 8439 | G/A | Arg/Arg |
| | 7347 | 8446 | A/G | Asn/Asp |
| | 7388 | 8487 | A/G | Ser/Ser |
| | 7436 | 8535 | C/T | Val/Val |

According to a preferred embodiment of the present invention a polynucleotide molecule encoding for an env protein of an infectious endogenous human retrovirus is provided, said polynucleotide molecule comprising a sequence selected from the group consisting of (a) a sequence with at least 98%, preferably 99%, still preferred 99.5%, identity to a sequence according to SEQ ID No 2, (b) a sequence which hybridizes under stringent conditions with a nucleotide sequence according to said SEQ ID No 2 and (c) a sequence which differs from said sequence (a) or (b) due to degeneration of the genetic code.

"Env" according to the present invention relates also to the sequence inserted into the deposited MERV-env plasmid as mentioned above or a fragment thereof.

It is known that retroviruses are "quasispecies" and sequence variation in a given virus population is given. Such quasispecies variations are, of course, included in the definition of the present viruses and of the sequences of the nucleic acid molecules according to the present invention as long as the infectivity of the virus population as a whole is given.

"Env" relates to the envelope protein which is a viral membrane protein mediating the binding of the virus particles to the cellular receptors enabling virus entry which is the first step in a new replication cycle. The env protein is particularly important for the ability to spread between cells and individuals (infectivity).

A further embodiment of the present invention relates to a polynucleotide molecule encoding for a pol protein of a HERV, whereby said polynucleotide molecule comprises a sequence selected from the group consisting of
(a) a sequence with at least 99%, preferably 99.5%, still preferred 99.8%, identity to a sequence according to SEQ ID No 3,
(b) a sequence which hybridizes under stringent conditions with a nucleotide sequence according to said SEQ ID No 3 and
(c) a sequence which differs from said sequence (a) or (b) due to degeneration of the genetic code. "pol" relates to the polymerase which is an enzyme with RNA dependant reverse transcriptase activity. Also this protein is important for a correct viral replication cycle.

"Pol" according to the present invention relates also to the sequence inserted into the deposited MERV-pol plasmid as mentioned above or a fragment thereof.

A still further aspect of the present invention relates to a polynucleotide molecule encoding for a gag protein of a HERV, whereby said polynucleotide molecule comprises a sequence selected from the group consisting of
(a) a sequence with at least 98%, preferably 99%, still preferred 99.5%, identity to a sequence according to SEQ ID No 4,
(b) a sequence which hybridizes under stringent conditions with a nucleotide sequence according to said SEQ ID No 4 and
(c) a sequence which differs from said sequence (a) or (b) due to degeneration of the genetic code.

The gag gene products have acquired the ability to be transported to the cell surface and abut on the cell membrane incorporating env proteins during this process. The gag gene codes for a long polyprotein which in a first step is cut from the long molecule chain and is then cut into a number of parts which are present around the RNA in form of capsomeres. Since these gag proteins are essential for the budding they are important for the infectious viral circle.

"Gag" according to the present invention relates also to the sequence inserted into the deposited MERV-gag plasmid as mentioned above or a fragment thereof.

A further embodiment relates to a polynucleotide molecule encoding for a pro protein of a HERV, whereby said polynucleotide molecule comprises a sequence selected from the group consisting of
(a) a sequence with at least 98%, preferably 99%, still preferred 99.5%, identity to a sequence according to SEQ ID No 5,
(b) a sequence which hybridizes under stringent conditions with a nucleotide sequence according to said SEQ ID No 5 and
(c) a sequence which differs from said sequence (a) or (b) due to degeneration of the genetic code.

The pro gene comprises 3 regions of particular interest:
1. dUTPase, dUTPase hydrolyses dUTP to dUMP and pyrophosphate.
2. prt retroviral Aspartyl-Proteinase
3. G_patch, α-glycine rich nucleic binding domain; A predicted glycine rich nucleic binding domain found in the splicing factor 45, SON DNA binding protein and D-type Retrovirus-polyproteins.

"Pro" according to the present invention relates also to the sequence inserted into the deposited MERV-prt plasmid as mentioned above or a fragment thereof.

Advantageously, a polynucleptide molecule is provided which comprises a sequence which is complementary to one of the above mentioned sequences according to the present invention. Therefore, not only the sequence according to the RNA strand present in the retrovirus particle is provided but also a sequence according to the cDNA sequence.

Still preferred, the polynucleotide molecule comprises a detectable label. In particular if the polynucleotide molecule is a fragment of the above defined sequence, the polynucleotide molecule can be used for the detection of infectious HERV in a sample. The term "detectable label" relates to any marker well known in the art, e.g. fluorescent, radioactive, enzymatic or chemical marker.

A further aspect of the present invention relates to a polynucleotide molecule coding for a ribozyme, which comprises two sections, each of which has a length of at least 10 to 15 base pairs and which are complementary to specific sequence sections of said above identified polynucleotide molecule according to the present invention so that said ribozyme complexes and cuts the mRNA transcribed by a natural infectious human endogenous retrovirus DNA. The publication by John M. Burg "Clearing the Way for Ribozymes" (Nat. Biotechnology 15:414-415 (1997)) relates to the general mode of function of ribozymes and is included herein by reference. The ribozyme will recognize the mRNA of infectious HERV by complementary base pairing with said mRNA. The ribozyme will then cleave and destroy the RNA in a sequence specific manner before the HERV is translated. After dissociation from the cleaved substrate the ribozyme will repeatedly hybridize with specific RNA molecules and act as specific endonuclease. In general, ribozymes may specifically be produced for inactivation of a certain mRNA even if not the entire DNA sequence which codes for the infectious HERV is known.

Ribozymes are particularly efficient if the ribosomes move slowly along the mRNA. In that case it is easier for the ribozyme to find a ribosome free site on the mRNA. For this slow ribosomes mutants are also suitable as a system for ribozymes (J. Jayburg (1997), Nature Biotechnology 414-415). A further possible way is also to use a varied form of a ribozyme, i.e. a minizyme. Minizymes are efficient particularly for cleaving larger mRNA molecules. A minizyme is a hammer head ribozyme which has a short oligonucleotide linker instead of the stem/loop II. Primer minizymes are particular efficient (Kuferbara et al. (1998), Nature Biotechnology 16, 961-965).

Here again the ribozyme comprises sequence sections which are complementary to "specific" sequence sections of the above defined polynucleotide molecule according to the present invention. It is sufficient if at least one of the two sequence sections is specific, meaning that this specific sequence section will only bind to an infectious HERV according to the present invention and not to already known and described non-infectious HERV sequences. Preferably, however, both sequence sections are specific for the above defined polynucleotide molecule according to the present invention, meaning that both sequence sections bind only infectious HERV sequences.

A further aspect of the present invention refers to a primer pair whereby the primers specifically hybridize to a polynucleotide molecule according to the present invention for an amplification reaction of a fragment of said polynucleotide molecule.

Here again the term "specifically" refers to primers which will only bind to the above defined polynucleotide molecule according to the present invention and not to any known already described HERV. It is sufficient, if only one of the primers is specific for the inventive polynucleotide molecule, however, preferably both primers bind specifically only to the inventive HERV polynucleotide molecule. This primer pair can be used for any detection reaction in order to detect the presence of a HERV in a sample, whereby the term "amplification reaction" relates to any reaction specifically amplifying a sequence corresponding to the above described HERV sequence according to the present invention. This may be, for example, a conventional PCR as well as RT-PCR which are both well known to a person skilled in the art. However, the primer pair can also be used to find further herein not defined parts of the infectious HERV provirus according to the present invention. The primer pair can furthermore be used to identify other infectious HERVs which comprise, at least partly, similar sequences to the sequence of the infectious HERV according to the present invention.

The skilled man in the art easily finds conditions wherein primers which are specific for the infectious HERV sequences according to the present invention (which e.g. differ from sequences of known (non-infectious) HERVs by only 1, 2 or 3 nucleotides) only hybridize or anneal to the sequences of the infectious HERVs according to the present invention, but not to e.g. the non-infectious HERV sequences known. Examples for such specific regions are e.g. the regions covering one or more of the mutations listed in Table 1. Further examples may be derived by the skilled man in the art e.g. by comparing the sequences of the present infectious HERV with the known (non-infectious) HERV-K sequences (e.g. HERV-K108).

A further aspect of the present invention relates to a biologically functional vector comprising a polynucleotide molecule according to the present invention. The biologically functional vector will comprise all elements necessary for efficiently expressing the polynucleotide molecule according to the present invention whereby these elements, e.g. the promoter will be selected according to the host into which the functional vector will be transfected and in which the polynucleotide molecule will be expressed, e.g. to produce a protein or polypeptide encoded by the present infectious HERV sequences. A person skilled in the art can select the optimal biologically functional vector without undue burden.

Still preferred, a biologically functional vector comprising a polynucleotide molecule as defined above according to the present invention in inverse orientation with respect to the promoter is provided. This vector allows the production of antisense mRNA which is complementary to the mRNA of the infectious HERV according to the present invention. The antisense mRNA will bind to the respective region of the infectious HERV mRNA and therefore block any further translation and production of viral proteins and therefore infectious viral particles. Hereby it is sufficient, if an essential part of the infectious HERV mRNA is blocked in order to block the production of a complete infectious viral particle, e.g. part of the gag, pol, pro or env mRNA. Therefore, said biologically functional vector can be used in cell cultures to stop the viral production as well as a gene therapy against or prevention of viral replication in a patient.

A further aspect of the present invention relates to a recombinant host cell stably transfected with said biologically functional vector according to the present invention as defined above. Here, the person skilled in the art will select the vector and host cell in order to achieve an effective result, e.g. high expression of the infectious HERV or fragments thereof. Transfection methods in order to produce a recombinant host cell are well known to the person skilled in the art and may comprise any electroporation, lipofectamin transfection, salt transfection etc. Depending on the vector which is transfected into the host cell, the host cell will either express viral peptides, proteins or particles or produce antisense mRNA.

Still preferred the host cell is a mammalian cell. This will allow the production of infectious HERV proteins or peptides with correct post-translational modifications. The mammalian cell may be, for example, from any human cell line.

A further aspect of the present invention relates to a method for producing an infectious human endogenous retrovirus or at least one fragment thereof comprising the steps of
(a) transfecting a host cell with a vector as defined above according to the present invention,
(b) selecting and cultivating cells which are stably transfected with said vector and
(c) isolating and purifying said retrovirus or said fragment.

Here again the above mentioned definitions and preferred embodiments apply, in particular with respect to the transfection step and the selection of the host cell and vector. The selection of stably transfected cells may be carried out according to any method well known in the art, e.g. selection with antibiotic resistance or optical selection. The term "fragment" relates to any peptide encoded by the above defined polynucleotide molecule according to the present invention. However, the fragment will preferably refer to a peptide which can be used as an antigen. To detect fragments which can be used as antigens known homologous fragments of corresponding HERVs or ERVs can be used, however, such fragments can also be detected by providing a sample of antibodies of infectious HERV, which sample can be taken of an infected patient, incubating said antibody or antibodies with one or more fragments of the infectious HERV proteins in conditions so that a binding between corresponding antigens and antibodies occur and identifying the respective fragments which have bound to antibodies of infectious HERV.

A further aspect of the present invention relates to an infectious human endogenous retrovirus comprising as RNA a polynucleotide molecule according to the present invention. Preferably the infectious HERV according to the present invention will comprise the complete polynucleotide molecule, e.g. comprising the pol, env, gag, pro genes as well as LTR sequences. However, it is also possible that the RNA comprises only one or a few, but not all of the above mentioned genes. It is important that the HERV is able to carry out a complete retroviral replication cycle and infect further cells.

Furthermore, an infectious human endogenous retrovirus is provided being encoded by a polynucleotide molecule as defined above according to the present invention.

A further aspect of the present invention relates to a preparation comprising an infectious HERV according to the present invention. The preparation may be a pharmaceutical preparation in which case preferably a pharmaceutically acceptable carrier is provided. However, the preparation may also be designed for diagnostic purposes as well as analytical or other purposes, e.g. to produce antibodies, to study the effects in animals etc. Of course, the preparation according to the present invention will comprise any additional substances depending on the use of the preparation. The preparation may comprise further virus particles, as non-infectious HERVs. However, at least one infectious HERV according to the present invention or a significant portion of the preparation leading to the overall infectivity of this preparation must be present.

A further aspect of the present invention relates to an env protein, a pol protein, a gag, a pro protein encoded by a polynucleotide molecule as defined above according to the present invention. These proteins can be used for any analytical, diagnostic or production methods and they will be provided in any form, e.g. with additional substances, depending on the use of the protein.

Furthermore a peptide is provided which is a specific fragment of said retrovirus as defined above according to the present invention. Here again, "specific" refers to any fragment which is not identical to a non-infectious HERV fragment already known. As mentioned above already the fragment may be any fragment of said retrovirus particle, however, preferably said fragment can be used as an antigen (e.g. a T or B cell epitope) and therefore be used in diagnostic methods as well as for the induction of the production of respective antibodies in a patient or animal and/or for the induction of specific T cell responses, both TH1 and TH2. The detection of such fragments can be carried out as described above.

The following fragments are examples of such antigens:
Fragments of the gag protein may be:

| | |
|---|---|
| LMQNEAIEQVRAICL, | (SEQ ID NO: 9) |
| IPYDWEILAKSSLSP, | (SEQ ID NO: 10) |
| ADQLLGIGQNWSTIS, | (SEQ ID NO: 11) |
| TISQQALMQNEAIEQ, | (SEQ ID NO: 12) |
| EKARKVIVELMAYEN, | (SEQ ID NO: 13) |
| MAYENANPECQSAIK, | (SEQ ID NO: 14) |
| PVLNKQNITIQATTT, | (SEQ ID NO: 15) |
| RSKFDKNGQPLSGNE, | (SEQ ID NO: 16) |
| LSGNEQRGQPQAPQQ, | (SEQ ID NO: 17) |
| QPPLSQVFQGISQLP, | (SEQ ID NO: 18) |
| EIIDKSRKEGDTEAW, | (SEQ ID NO: 19) |
| VSTKNLIKL, | (SEQ ID NO: 20) |
| GIGQNWSTI, | (SEQ ID NO: 21) |
| QYGPNSPYM, | (SEQ ID NO: 22) |
| CPVLNKQNI, | (SEQ ID NO: 23) |
| LTVWNDWAI, | (SEQ ID NO: 24) |
| KFDKNGQPL, | (SEQ ID NO: 25) |
| GKCYNCGQI, | (SEQ ID NO: 26) |
| HLKKNCPVL, | (SEQ ID NO: 27) |
| GRKGNIIPL, | (SEQ ID NO: 28) |
| FSIKMLKDM | (SEQ ID NO: 29) |

Fragments of the env protein may be:

| | |
|---|---|
| PAVDSDLTESLDKHK, | (SEQ ID NO: 30) |
| WNSQSSIDQKLANQI, | (SEQ ID NO: 31) |
| VSMDRPWEASPSVHI, | (SEQ ID NO: 32) |
| PAVQNWLVEVPTVSP, | (SEQ ID NO: 33) |
| LRPRVNYLQDFSYQR, | (SEQ ID NO: 34) |
| NTEVLVWEECVANSA, | (SEQ ID NO: 35) |
| SAVILQNNEFGTIID, | (SEQ ID NO: 36) |
| QFYHNCSGQTQSCPS, | (SEQ ID NO: 37) |
| NRSKRFIFTLIAVIM, | (SEQ ID NO: 38) |
| PYMLVVGNI, | (SEQ ID NO: 39) |
| IFKASKAHL, | (SEQ ID NO: 40) |
| KTIGSTTII, | (SEQ ID NO: 41) |
| GYHYPPICL, | (SEQ ID NO: 42) |
| SYQRSLKFR, | (SEQ ID NO: 43) |
| KGKPCPKEI, | (SEQ ID NO: 44) |
| VEVPTVSPI, | (SEQ ID NO: 45) |
| SLRPRVNYL, | (SEQ ID NO: 46) |
| TFNWQHRIL | (SEQ ID NO: 47) |

Preferably, such peptide fragments contain at least 6 amino acid residues with at least one residue being specific for the present infectious HERV sequences, especially at least one of the amino acid residues not being present in the (non-infectious) HERV-K (HERV-K108). More preferred these peptides have a length from 7 to 15 amino acids, especially from 8 to 11. Such peptide fragments of these lengths are preferably fragments of the above mentioned gag and env fragments.

A further aspect of the present invention relates to an antibody which is directed against an antigen derived from said retrovirus as defined above according to the present invention. The production of antibodies towards any specific antigen may be carried out according to any method well known in the state of the art, e.g. by immunization of an animal and producing the antibodies in cell culture. The term "antibody" refers to any form of antibody, e.g. monoclonal, polyclonal, humanized antibody etc. The antibodies directed against antigens from the infectious HERV according to the present invention can be used in immunizing methods, diagnostic methods or therapeutic methods.

Preferably, an antibody fragment is provided which is directed against an antigen derived from said retrovirus as defined above according to the present invention. Such antibody fragments may be for example Fa, F(ab)$^2$ or Fv which are capable of binding an epitopic determinant. Furthermore, single chain antibodies are comprised by the term "antibody fragment". These antibody fragments can be used as described above for the antibodies, however, due to their smaller size they may show advantages with respect to stability, production etc. Also here, the antibody fragment is specific, meaning that the antibody fragment comprises a sequence specific to infectious HERV according to the present invention.

A further aspect of the present invention relates to a solid support which has attached to its surface said antibodies defined above according to the present invention or said antibody fragments as defined above according to the present invention. The solid support according to the present invention may be of any size or shape, e.g. in the form of a flat slide, microtiter plate, chip, filter, column, membrane etc. and may be made of any material generally used for solid supports, e.g. modified or unmodified glass, polymeric material etc. Hereby the antibody or antibody fragment can be attached to the complete surface of the solid support. However, it may also be attached in localized regions, as for example spots. Also the quantity in which the antibody is bound to said solid support may vary according to the size of the antibody or antibody fragment. Of course, for high throughput assays it will be advantageous to use micro array chips on which the antibodies or antibody fragments are bound in high density. The selection of the solid support and the mode of attachment of the antibody to its surface will depend on the use of said solid support, e.g. for preparation, purification methods, detection methods, etc. and a person skilled in the art will be able to select the most appropriate solid support and the optimum mode of attachment of said antibody or antibody fragment to said solid support.

A further aspect of the present invention relates to a method for diagnosing cancerous cells comprising the steps of
(a) providing a sample of said cells to be tested or supernatant thereof,
(b) analyzing whether or not said infectious endogenous retrovirus according to the present invention as described above or fragment thereof is present in said sample whereby
(c) the presence of said retrovirus or fragment thereof in said sample diagnoses cancerous cells.

The term "cancerous cells" refers to malignant tumor cells. It has been surprisingly found that the infectious HERV according to the present invention is related to the transformation of cells into cancerous cells, especially melanomas. Therefore, by detecting the presence of said infectious HERV it is possible to diagnose cancerous cells already at a very early stage. Therefore, the term "diagnosing cancerous cells" includes also diagnosing cells which will be transformed into cancerous cells, however, with conventional methods these cells would not yet be diagnosed as transformed.

However, it is not necessary to detect the complete infectious endogenous retrovirus. It is sufficient to detect at least one specific fragment thereof. Here again, the term "specific" refers to a fragment containing a sequence which differs from the sequences of the known non-infectious HERVs. The clear detection method may be carried out according to any protocol known in the art whereby it is possible to detect said infectious HERV or fragment thereof on DNA, RNA or protein level. It is further possible to determine the stage of cancer by determining the amount of infectious HERV.

Preferably, said analyzing step comprises an antigen-antibody reaction using an antibody or antibody fragment as defined above according to the present invention in order to detect proteins or protein fragments of said retrovirus. Here, any known antigen-antibody reaction may be carried out, e.g. on solid support, in liquid phase, by sandwich-ELISA, etc. It is, of course, possible to detect antibodies in said sample, however, since the production of antibodies may vary, it is preferred to detect an antigen in said sample by providing one or more specific antibodies whereby these antibodies may be bound to a solid support and/or comprise a label which may be detected and quantified.

According to a preferred method said analyzing step comprises detecting the polynucleotide sequence of said retrovirus and a fragment of the polynucleotide sequence specific for said retrovirus, respectively, whereby a hybridization reaction or amplification reaction is carried out using a polynucleotide as defined above according to the present invention. Hereby, the term "polynucleotide sequence" comprises RNA sequences, e.g. the polynucleotide molecule derived from the transcription of the respective DNA or the polynucleotide molecule present in the virus particle, as well as DNA, e.g. cDNA resulting from the reverse transcriptase reaction thereafter, whereby the cDNA may be still present in the virus particle or also the DNA already integrated into the host DNA. Therefore, said amplification reaction will comprise PCR as well as RT-PCR. Therefore, the above mentioned primer pair will preferably be used.

Advantageously, said polynucleotide sequence is transformed into cDNA in a reverse transcription step prior to said hybridization step and amplification reaction, respectively. Said hybridization step will be preferably carried out with one of the above defined fragments of said polynucleotide molecule according to the present invention as mentioned above. Hereby it is, of course, possible to use labeled fragments or labeled nucleotides, e.g. retroactive nucleotides in order to easily detect and quantify, respectively, said polynucleotide sequence.

According to a further preferred method said analyzing step comprises
(a) providing cells devoid of said endogenous retrovirus,
(b) adding said supernatant of said sample to said cells,
(c) cultivating said cells and
(d) detecting a polynucleotide molecule as defined above according to the present invention in the DNA of said cells.

Since the HERV according to the present invention is infectious, the supernatant of said sample—if it comprises an infectious HERV—will infect the cells devoid of said endogenous retrovirus. After infection the infectious HERVs will integrate into said cells and further HERV particles will be produced. After cultivating said cells, therefore, the integrated polynucleotide molecule of the infectious HERV as defined above will be detectable in the DNA of said cells. This is a very reliable and quick method for detecting infectious HERVs. Again, the detection of said polynucleotide molecule may be carried out by a hybridization step and amplification reaction, respectively.

Preferably said cells are non-human cells. Since non-human cells do not comprise HERVs, the detection of a HERV polynucleotide molecule in said human cells will be a clear method of detecting infectious HERV particles. Preferably, said non-human cells are bovine cells. Infectivity of the virus particles with respect to these non-human cells is also a way of defining infectivity according to the present invention.

Still preferred said sample is a skin tissue sample from a patient. Since said infectious HERVs preferably infect skin tissue cells, a sample of a skin tissue is preferably used in order to detect said infectious HERVs.

Still preferred, said sample comprises melanocytes. Since said infectious HERVs are related to cancerous cells a sample comprising melanocytes is a preferred sample for detecting infectious HERVs according to the present invention.

According to a preferred embodiment of the present invention a method is provided for diagnosing cancer in a patient comprising the steps of
(a) providing a sample of said patient to be tested,
(b) analyzing whether or not at least one antibody as defined above or antibody fragment as defined above according to the present invention is present in said sample whereby
(c) the presence of said antibody or fragment thereof in said sample diagnoses cancer.

Here again, the same definitions and preferred embodiments as mentioned above apply.

Preferably said sample is a blood sample of said patient. A blood sample is very easily and quickly taken from a patient without necessity of costly apparatuses. Furthermore, it is possible to diagnose an unlimited amount of samples in a very short time. As mentioned above for high throughput assays it is preferable to use microarrays.

According to an advantageous method said analyzing step comprises an antigen-antibody reaction using an antigen derived from said retrovirus as defined above according to the present invention. Here again, the above mentioned definitions and preferred embodiments apply.

According to a further advantageous embodiment a kit is provided for diagnosing cancerous cells according to the method as mentioned above according to the present invention comprising
(a) a first reagent comprising a polynucleotide molecule as defined above according to the present invention, an antibody as defined above according to the present invention or an antibody fragment as defined above according to the present invention or a solid support as defined above according to the present invention and
(b) as a positive control a second reagent comprising a polynucleotide comprising a sequence which is complementary to the sequence of said polynucleotide in said first reagent or a retrovirus as defined above according to the present invention, an env protein as defined above according to the present invention, a pol protein as defined above, a gag protein as defined above or a peptide as defined above according to the present invention. Here again, the same definitions and preferred embodiments as described above apply. Of course, it is also possible to provide additionally to the first reagent a further solid support without attached antibodies or antibody fragments. In this case the antibody or antibody fragment as well as the mode of attachment can be varied.

According to a further embodiment of the present invention a kit for carrying out a method for diagnosing cancer in a patient as described above is provided comprising
(a) a first reagent comprising an antigen derived from said retrovirus as defined above and
(b) as a positive control a second reagent comprising an antibody according to the present invention or an antibody fragment as defined above specific for said antigen in said first reagent.

Here again the same definitions and preferred embodiments as described above apply.

Preferably, said antigen is labeled with a detectable marker. This marker may be for example radioactive, fluorescent, an enzymatically or chemically detectable marker.

Such markers are well known in the state of the art and the person skilled in the art will be able to select the optimal marker.

Still preferred, said antigen is immobilized to a solid support. This allows an easy handling of said kit and the method can be carried out immediately without prior preparations.

According to a further embodiment of the present invention a PNA molecule is provided which comprises a base sequence complementary to the sequence of said polynucleotide molecule as defined above according to the present invention. PNA (peptide nucleic acid) is a DNA like sequence, the nucleic basis being bound to a pseudo peptide backbone. PNA generally hybridizes with complementary DNA, RNA or DNA polymers by Watson-Creek base pair and helix formation. The peptide backbone ensures a greater resistance to enzymatic degradation. The PNA molecule thus is an improved antisense agent.

Here, the advantage lies in that neither nucleases nor proteases are capable of attacking a PNA molecule. Therefore, the PNA molecule is highly stable, if it is bound to a complementary sequence, since it comprises a sufficient steric blocking of DNA and RNA polymerases, reverse transcriptase, telomerase and ribosomes (Buga et al, "Cell Penetrating DNA Constructs Regulate Alanin Receptor Levels and Modify Transmission in vivo", Nature Biotechnology 16:857-861 (1998)).

As in the case of the antisense RNA, if the PNA molecule comprises the above defined sequence it will bind to the DNA/RNA or to a site of the DNA/RNA respectively, which codes for infectious HERV peptides. In this way, the PNA molecule will inhibit the transcription of the virus. The PNA molecule is prepared synthetically, e.g. by aid of the T-boc technique, since it is neither transcribed nor translated.

The present invention also relates to the use of anti-retroviral substances for preparing a medicament to treat melanoma. The present invention therefore provides a method for treating patients having or being at risk of developing melanoma comprising administering an effective amount of substances acting against retroviruses, e.g. substances which inhibit replication and polymerization of retroviral (infectious HERV) genomes. Examples of such treatment are e.g. known for the treatment of HIV infections.

Preferably, a pharmaceutical composition is provided comprising a polynucleotide as defined above according to the present invention, a vector as defined above according to the present invention, an antibody as defined above, an antibody fragment as defined above and a PNA molecule as defined above, respectively, and a pharmaceutically acceptable carrier. Of course, the pharmaceutical composition may comprise any further molecules or substances useful for a therapeutic method. The pharmaceutical composition may for example be provided as a skin cream or lotion, which may for example be used as an after sun lotion in a preventive manner.

Preferably, the pharmaceutical composition further comprises at least one antiviral substance, especially anti-retroviral substances. These may be any substances well known in the art, for example the agents used in known triple anti-retroviral therapy, see for example Bartlett J A, DeMasi R, Quinn J, Moxham C, Rousseau F. Overview of the effectiveness of triple combination therapy in antiretroviral-naive HIV-1 infected adults. AIDS. 2001 Jul. 27; 15(11):1369-77; Marimoutou C, Chene G, Mercie P, Neau D, Farbos S, Morlat P, Ceccaldi J, Dabis F. Prognostic factors of combined viral load and CD4+ cell count responses under triple antiretroviral therapy, Aquitaine cohort, 1996-1998. J Acquir Immune Defic Syndr. 2001 Jun. 1; 27(2):161-7, which are incorporated herein by reference.

According to a further embodiment of the present invention a sun cream is provided which comprises a polynucleotide as defined above according to the present invention, an antibody, an antibody fragment as defined above and a PNA molecule as defined above, respectively, and at least one UV-protection substance. Therefore, applying a sun cream with these substances will prevent or inhibit the production of or infection by infectious HERV according to the present invention.

Preferably, said sun cream further comprises at least one antiviral substance. Here, the same antiviral substance as mentioned above for the pharmaceutical composition will be preferred.

According to a further embodiment of the present invention a vaccine is provided which comprises as an antigen an attenuated retrovirus as mentioned above, an env protein, a pol protein, a gag protein or a peptide as defined above according to the present invention, respectively, and optionally an adjuvant. Such a vaccine when applied to a patient will induce the production of antibodies and/or T cells, which can inhibit infectious HERVs according to the present invention. Therefore, such a vaccine is a highly effective substance for treating infectious HERV infections. The production of vaccines against retroviruses is described in "Hyperattenuated Recombinant Influenza A Virus Nonstructural-Protein-Encoding Vectors Induce Human Immunodeficiency Virus Type 1 Nef-Specific Systemic and Mucosal Immune Responses in Mice", Boris Ferko, Jana Stasakova, Sabine Sereinig, Julia Romanova, Dietmar Katinger, Brigitte Niebler, Hermann Katinger, and Andrej Egorov. Journal of Virology, October 2001, p. 8899-8908, Vol. 75, No. 19, which is incorporated herein by reference.

BRIEF DESCRIPTION OF THE DRAWINGS

The present invention is described in more detail with the help of the following examples and figures to which it should not, however, be limited.

In the drawings:

FIG. 3 shows the expression of the retroviral pol gene in melanomas.

FIGS. 7A and 7B show the transfer of supernatants from melanoma particle exposed MDBK cells to uninfected MDBK cells.

FIGS. 8A and 8B show the vector pCR4Topo (SEQ ID NOs:48 and 49) as well as the gag (SEQ ID NO:50), prot (SEQ ID NO:51), pol (SEQ ID NO:52) and env (SEQ ID NO:53) primers.

DESCRIPTION OF ILLUSTRATIVE EMBODIMENTS

EXAMPLES

Example 1

Figure 1A:
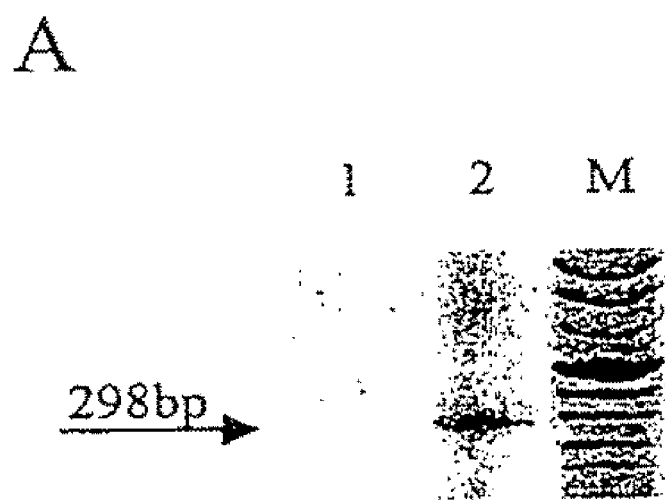
FIG. 1 shows the characterization of particle preparations from melanoma cell supernatants.

Human Melanoma Cells Contain RT Activity in Their Supernatants

To detect extracellular virions, supernatants from the melanoma cell lines SKMel-28, SKMel-1, 518A2 were analyzed, as well as primary melanoma cells for pelletable RT. Supernatants from cultured human neonatal melanocytes (NHEM) served as controls. Cell-free supernatants from approximately $10^6$ cells were concentrated by centrifugation. The RT activity of the resulting pellets was analyzed by F-PERT assay.

Supernatants from melanoma cell lines, and normal human melanocytes were centrifuged at 3000×g at 4° C. and sterile-filtered through a 0.22 µm low-protein membrane (Nunc) to remove cells and cellular debris. The clarified supernatants were centrifuged for 20 min at 250000×g at 4° C. in a Beckman SW50.1 rotor. Pellets were rinsed with phosphate-buffered saline (PBS) and centrifuged for 15 min at 250000×g and resuspended. The resulting particle suspensions were used as an enzyme source for RT assays.

Pelleted particles derived from 4 ml cell-free supernatants of approximately $10^6$ cells were analyzed. RT activity was determined by fluorescent probe-based product enhanced RT (F-PERT) assay as described, with modifications. First, pellets were suspended in lysis buffer (Roche). Then RT was performed, using the suspended pellet as source of enzyme, the primer 3'A10 (5'-CACAGGTCAAACCGCCTAG-GAATG-3' (SEQ ID NO:54)), and 0.3 µg MS2-RNA as a template (Roche #165948). To limit unspecific reverse transcription, 0.5 µg calf-thymus DNA (Sigma #D4522) was added. After incubation at 42° C. for 1 h, a 5 µl aliquot of this reaction was amplified by real-time PCR, by adding 25 µl TaqMan Universal PCR Master Mix (Applied Biosystems #430-4437), 1 µl of the primers 3'A10 and 5'A 11 (5'-TCCT-GCTCAACTTCCTGTCGAG-3' (SEQ ID NO:55)) at a concentration of 10 µM each, 1 µl F-PERT probe (genXpress, 10 µM, 5'(FAM)-TCTTTAGCGAGACGCTACCATGGCTA-(TAMRA)3' (SEQ ID NO:56)), and 17 µl AD. The resulting mixture was then amplified by incubating 10 mins at 95° C., followed by 40 cycles at 94° C. for 20 sec and 64° C. for 1 min, in a SD 7700 (Perkin Elmer). The calibration curve was generated by plotting the RT activity of a serial dilution of Moloney Murine Leukemia Virus (M-MLV) RT (Superscript II Gibco #18064-014). Alternatively, detection of reverse transcriptase was performed with a commercially available reverse transcription assay (Boehringer Mannheim). In this procedure, dioxigenin (DIG) and biotin-labeled nucleotides synthesized by the reverse transcriptase are incorporated into the DNA molecule. Biotion-labeled DNA is then captured to the streptavidin coated surface of the microtiter plates. In a subsequent step, an antibody to DIG conjugated to peroxidase is bound to the dioxigenin-labeled DNA. In the final step, the peroxidase substrate ABTS and a substrate enhancer were added. The absorbance of the samples was determined using a microtiter plate reader. The calibration curve was generated by plotting a serial dilution of an HIV-1 derived RT with defined activity.

Supernatants were found to contain a fluctuating yet continuously present RT activity, corresponding to the activity of up to 10000 µunits of M-MLV RT (Superscript II, Gibco) per ml supernatant. On the other hand, supernatants from cultured melanocytes did not contain detectable RT activity (detection limit $10^{-1}$ µunits). The fact that supernatants derived from melanoma cells but not from melanocytes contain pelletable RT activity shows that melanoma cells contain proviral sequences with sufficient genetic information to form particles containing a functional RT. Since no RT activity was detected in the supernatants of melanocytes, production of particles containing RT appears to be activated during transformation of melanocytes to malignant cells.

Example 2

Human Melanoma Cell Derived Particles Package Sequences with High Homology to HERV-K Retroviral pol genes are generally the most conserved sequences among retroviruses. In an attempt to analyze the particle preparations on a molecular level, a sequence was amplified by using degenerate primers corresponding to conserved sequences of the pol gene. Particle preparations of the melanoma cell line 518A2 and SK-Mel28 were used for RT-PCR analysis. Particles were treated with DNase, to remove contaminating traces of genomic DNA.

Oligonucleotide primers 3'ABDPOLS 5'dCATTCCT-TGTGGTAAAACTTTCCA[T/C]TG 3' (SEQ ID NO:57) and 5'ABDPOLAS 5'dCCCCTTGGAATACTCCTGTTTT [T/C]TG 3' (SEQ ID NO:58) (Codon Genetic Systems, Austria), derived from conserved regions within the retroviral reverse transcriptase (RT), were adopted from Medstrand and Blomberg. In order to release viral RNA, the particle suspension was transferred to a 0.5 ml polypropylene microcentrifuge tube (Sörensen Inc., USA). Then 10 µl of sterile water containing 0.1% Triton X-100 and 10 U RNase inhibitor (Gibco) was added and incubated at 65° C. for 10 min. The reverse transcription was performed in the same tubes. A mixture containing 50 mM Tris-HCl buffer pH 8.3, 50 mM KCl, 7.5 mM MgCl$_2$, 5 mM DTT, 1 mM dNTPs, 20 pmol primer 3 'ABDPOLA, 10 U RNase inhibitor and 100 U of Superscript II RT (Gibco) in a final volume of 20 µl was added while the tubes were kept on ice. The reaction was performed at 42° C. for 45 min.

For PCR, the reaction mixture contained 10 mM Tris-HCl buffer pH 8.3, 50 mM KCl, 1.5 mM MgCl$_2$, 0.005% (w/v) gelatin, 0.2 mM dNTPs, 25 pmol of 3'ABDPOLS and 5'ABD-POLAS, 10 µl of the reverse transcription reaction and 1.25 U Taq polymerase (Boehringer Mannheim) in a final volume of 50 µl. The reaction mixes were overlaid with mineral oil and subjected to 3 thermal cycles of denaturation at 92° C. for 45 s, primer annealing at 45° C. for 45 s and elongation at 72° C. for 60 s, followed by 45 cycles at 92° C. for 45 s, 55° C. for 45 s and 72° C. for 60 s. 10 µl of each amplification product, were analyzed by electrophoresis in a 1.5% agarose gel and visualized by ethidium bromide staining. An aliquot of the amplification product was cloned and sequenced.

RT-PCR of these preparations revealed the anticipated amplification products of 298 nucleotides. Since no amplification products were obtained when RT was omitted, possible DNA contaminations can be excluded (FIG. 1a). (A) RT-PCR. Particle preparations of the melanoma cell line Mel-Juso were treated with DNase and used for analysis. PCR (lane 1) or RT-PCR (lane 2) with degenerate primers corresponding to sequences that are conserved in retroviral polymerase (pol) genes was performed; M, molecular weight marker (Boehringer Mannheim VIII). No amplification products were obtained in the control reactions without RT, demonstrating the absence of contamination with DNA (lane 1). In contrast, RT-PCR revealed the anticipated amplification products of 298 nucleotides (lane 2). (B) Immunoblotting. Particle preparations from SK-Mel28 supernatants were separated by SDS-PAGE, blotted and HERV-K-specific proteins were detected with antiserum recognizing env (lane 1), gag (lane 3) and the corresponding pre-immunesera, pre-env (lane 2) and pre-gag (lane 4). Molecular weight is indicated to the left. In addition, RT-PCR of the GAPDH gene was negative, reflecting the lack of contamination with cellular mRNA (data not shown). The amplification product was cloned into an expression vector and sequenced. Sequence analysis revealed that the amplified fragment shows high homology to the corresponding pol region of endogenous retrovirus HERV-K. Translation of the obtained nucleotide sequence revealed the amino acid sequence IKKKSGKWRMLTDL-RAINSVIQPMGALQPGLPSPAIIPKN-WPLVVIDLKDSFFTIPL ADQDCEWFAFIIPAVNNLQ-PAKHF (SEQ ID NO:59). This sequence is highly homologous with the corresponding sequences of the HERV-K HML2 and HML3 families. Within these groups the highest identity (90%) was observed for clone NMWV5 (GenBank accession AF0115998). Homology to sequences of type A, B and C retroviruses was less than 70%. The sequence analysis excludes contamination with any known non-human retrovirus and suggests an endogenous origin of the packaged RNA.

Example 3

Human Melanoma Derived Particles Contain Mature Gag and Env Proteins

Particles derived from SK-Mel28 melanoma cells were purified on iodixanol-cushions and analyzed for the presence of HERV-K-specific env and gag proteins in Western blots.

Iodixanol-cushion purified particles from SK-Mel28 supernatants were pelleted, resuspended in PBS and analyzed. The amount of soluble proteins was quantified by means of a modified Bradford analysis (Bio-rad, Richmond Calif.). 5 µg of total protein was applied per lane and separated by SDS-PAGE (10%). Proteins were transferred to PVDF membranes (Millipore, Bedford, Mass.) by Western blotting, and generated blots were incubated with the gag- and env-specific antisera. The membranes were washed twice with blocking solution and HERV-K-specific proteins were detected with an alkaline-phosphatase-conjugated second-step antibody.

Figure 1B:
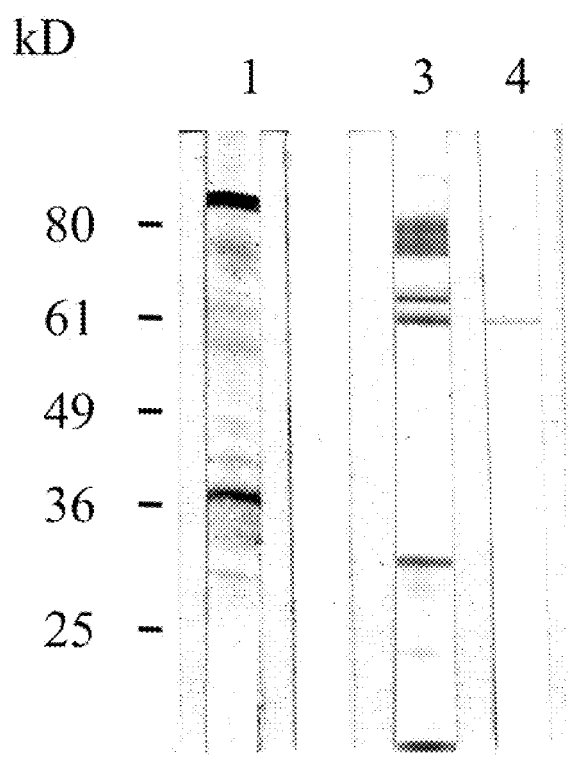

The envelope (env) gene of retroviruses displays an ORF for the surface protein (SU) and a membrane spanning protein (TM). The env precursor is usually cleaved into the SU and TM subunits before translocation to the cell surface and incorporation into virus particles. To determine whether the env protein is present on the particles, immunoblotting with an antiserum recognizing the TM domain was performed. As shown in FIG. 1b two bands are visible in the Western blot. The upper band corresponds to the precursor migrating at approximately 80 to 90 kDa. In addition, a lower band migrating at approximately 37 kDa is visible, suggesting cleavage of the precursor into subunits.

Immunoblotting with an HERV-K anti-gag antiserum revealed a double band at approximately 76 kDa, corresponding to gag precursors, as well as processed intermediate gag proteins at approximately 61 kDa, 30 kDa and one band migrating with the front (less than 19 kDa). The 30 kDa protein corresponds to the putative major core protein of HERV-K. The presence of processed gag proteins in the Western blots indicates a functional protease.

Example 4

Human Melanoma Cells Produce Retrovirus-Like Particles

To confirm the presence of particles electron microscopy (EM) was performed.

15 µl aliquots of iodixanol-density gradient purified particle suspensions from SK-Mel28 supernatants were applied on Formvar coated grids and left there for 15 min. Excess suspension was removed from the edges of the grids by filter paper. The grid with the remaining sample was air dried for 1 h. The sample was either directly exposed to 1% uranyl acetate for negative staining or, for immunoelectron microscopy, fixed in paraformaldehyde-lysine-periodate for 15 min, rinsed in distilled water, quenched in PBS/1% BSA and incubated in anti-env antiserum diluted 1:25 in PBS/1% BSA for 1 h at RT. After washing, the grid was exposed to 5 nM colloidal gold conjugated rabbit anti-goat antibody (British Biocell, Cardiff, UK) diluted 1:50 in PBS/1% BSA for 1 h. After fixation in 2.5% glutaraldehyde, washing and negative staining with 1% uranyl acetate, the grid was left to air dry. All grids were examined with a JEOL 1010 electron microscope.

For electron microscopy, immunoblotting and infection studies, cell-free supernatants were purified on iodixanol density gradients or cushions. Iodixanol is an iodinated, nonionic density gradient medium (Nycomed Pharma, Oslo, Norway). It has a low viscosity and provides iso-osmotic conditions up to densities of 1.32 g/ml. The supernatants were overlaid on a cushion of 5 ml 50% iodixanol. The tubes were centrifuged in an SW28 rotor at 45000×g for 2 h at 4° C. and the supernatant was removed from the tubes by suction, leaving a volume of 4 ml of the medium in proximity of the cushion. This fraction was harvested, pelleted in a SW41 rotor at 150000×g for 90 min at 4° C., resuspended in PBS and analyzed. Alternatively, for further purification the cushion-derived fraction was loaded on iodixanol density gradients, and the fraction corresponding to a density of approximately 1.16 g/ml was harvested. The harvested fractions were diluted in PBS and pelleted in a SW41 rotor at 150000×g for 90 min at 4° C. and resuspended in PBS.

Figure 2:
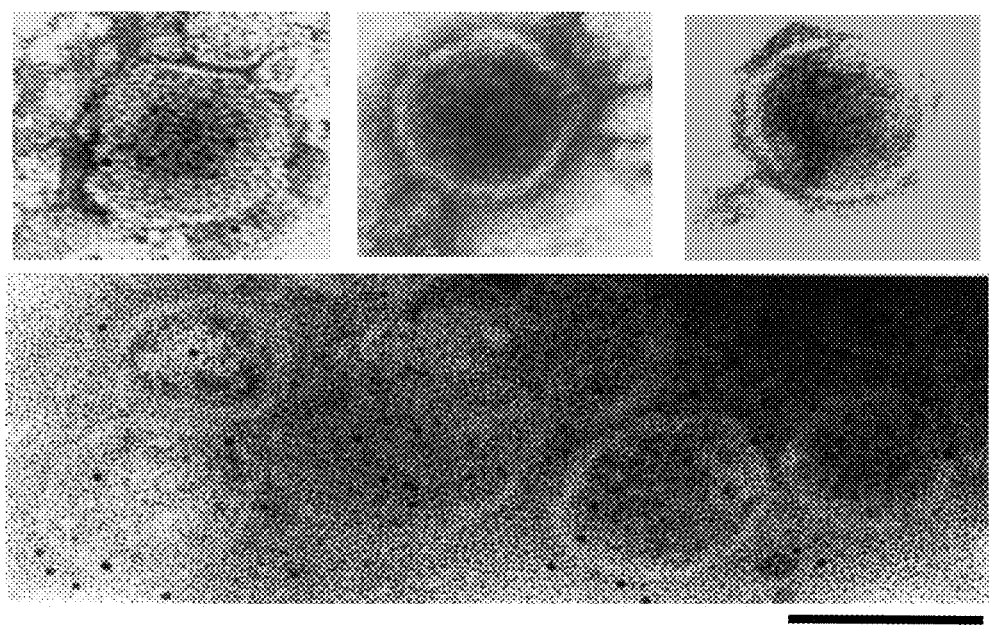
FIG. 2 shows an electron microscopy of melanoma cell-derived supernatants.

Pellets were partially purified on iodixanol-cushions (FIG. 2, upper part). Alternatively, these fractions were further purified on iodixanol density-gradients (FIG. 2, lower part). These preparations were analyzed by immunelectron microscopy using an env-specific antiserum and a colloidal gold conjugated reporter antibody. EM analysis of these preparations revealed the presence of retrovirus-like particles characterized by membrane bound spherical structures with diameters ranging between 80 and 120 nm. The presence of immunogold on the particles indicates that the env protein is present in the envelope.

Example 5

The Pol Gene is Expressed in Tumor Cells Derived from Melanomas

The integration sites of human endogenous retroviral elements have been found to be distributed over the whole human genome. For example, the HERV-K family was reported to be present in approximately 30 copies per human haploid genome. Based on the observation that melanoma cells (but not melanocytes) produce retrovirus-like particles, it can be hypothesized that the formation of virus-like particles might be due to the activation of retroviral genes that are usually repressed. Therefore the cloned pol sequence derived from the particle preparations was used as a probe and looked for expression of this sequence in the cytoplasm of melanoma cells by in situ hybridization.

Touch preparations of a nevus, primary melanoma, and melanoma metastasis were made by dipping freshly excised tissue on coated slides (DAKO, Biotek Solutions). Slides were fixed in 4% paraformaldehyde for 20 mins, washed in PBS, dehydrated through graded alcohols to absolute ethanol, and were air dried.

The hybridization mixtures consisted of Hybrisol VI (Oncor, Gaithersburg) and DIG-labeled cDNA probes, giving a final concentration of 2 ng/μl. Slides were covered with glass coverslips and sealed with Gelbond (ICN). Probe and cellular material were denatured by heating to 80° C. for 5 mins. Hybridization was carried out at 37° C. overnight in a humid chamber. After removal of the coverslips the slides were washed at 46° C. three times with 50% formamide/2× SSC, once with 2× SSC for 10 mins, followed by a single wash step in 2× SSC containing 0.1% NP40 for 10 mins. Signal detection was performed after a blocking step in 1% blocking reagent (Boehringer Mannheim) of 30 mins at 37° C. by incubation with anti-DIG antibody, conjugated to rhodamine at a dilution of 1:10 in 1% blocking reagent for 30 mins at 37° C. in a humidified box. After extensive washings in PBS, slides were counterstained with 10 μg/ml DAPI for 20 mins and visualized with a Zeiss fluorescence microscope using a triple bandpass filter and software from PSI.

To determine the specificity of the pol sequence for melanoma, touch preparations of a nodular melanoma were analyzed, a lymph node metastasis, and a cutaneous metastasis that had been surgically removed from melanoma patients. As shown in FIG. 3 (Touch preparations from primary melanoma (a), lymph node metastasis (b), cutaneous metastasis (c), nevus (d), and a tumor free sentinel lymph node (e) surgically removed from patients were analyzed by in situ hybridization with probes specific for nucleotide sequences of the pol gene (POL), melanoma inhibiting activity gene (MIA), and the influenza virus nucleoprotein (FLU). Nucleotide sequences of the pol and the melanoma inhibiting activity genes are found in primary melanoma and lymph node and cutaneous metastases but not in the nevus and tumor free lymph node), high copy numbers of the pol sequence were found in tumor cells of all melanoma preparations tested. In comparison, cells derived from the lymph node and the benign nevus of healthy individuals were negative. A probe specific for the nucleoprotein gene of influenza virus was always negative. As a positive control, a probe recognizing the melanoma-inhibiting activity gene was used. The rate of tumor cells expressing the pol gene was in the range of 60-90%, a percentage similar to the one obtained with the melanoma-inhibiting activity specific probe. The observation that the sequences are not found in all tumor cells might be due to the sensitivity of the assay and variations in the expression levels.

Example 6

Retroviral Gag, cORF, and Env Proteins are Expressed in Melanomas

To determine whether HERV-specific proteins were detectable in melanoma cells, immunofluorescence analysis with antisera recognizing the gag, cORF and env proteins of HERV-K was performed.

Cells grown on chamber slides, as well as touch preparations from a nevus and primary melanoma on coated slides (DAKO) were fixed in 4% paraformaldehyde for 20 mins, washed in PBS and dehydrated through graded alcohols to absolute ethanol and air dried. In addition, five micrometer sections prepared from routinely processed paraffin wax blocks of a nevus and melanoma were placed on coated slides (DAKO). The tissues were dewaxed in xylene, rehydrated by sequential immersion in graded ethanols and PBS and subsequently permeabilised by microwave treatment.

Immunofluorescence staining was performed by incubating chamber slides, touch preparations, and paraffin sections with HERV-K-specific antibodies at a dilution of 1:100 for 1 h at 37° C. in a humidified box, followed by washing three times with PBS and subsequent incubation with Alexafluor-488-conjugated antibodies at a dilution of 1:200 for 1 h at 37° C. Counterstaining was performed by mounting in Vectashield containing DAPI (Vector). Preparations were analyzed by using a Zeiss fluorescence microscope with appropriate filters.

Figure 4A:
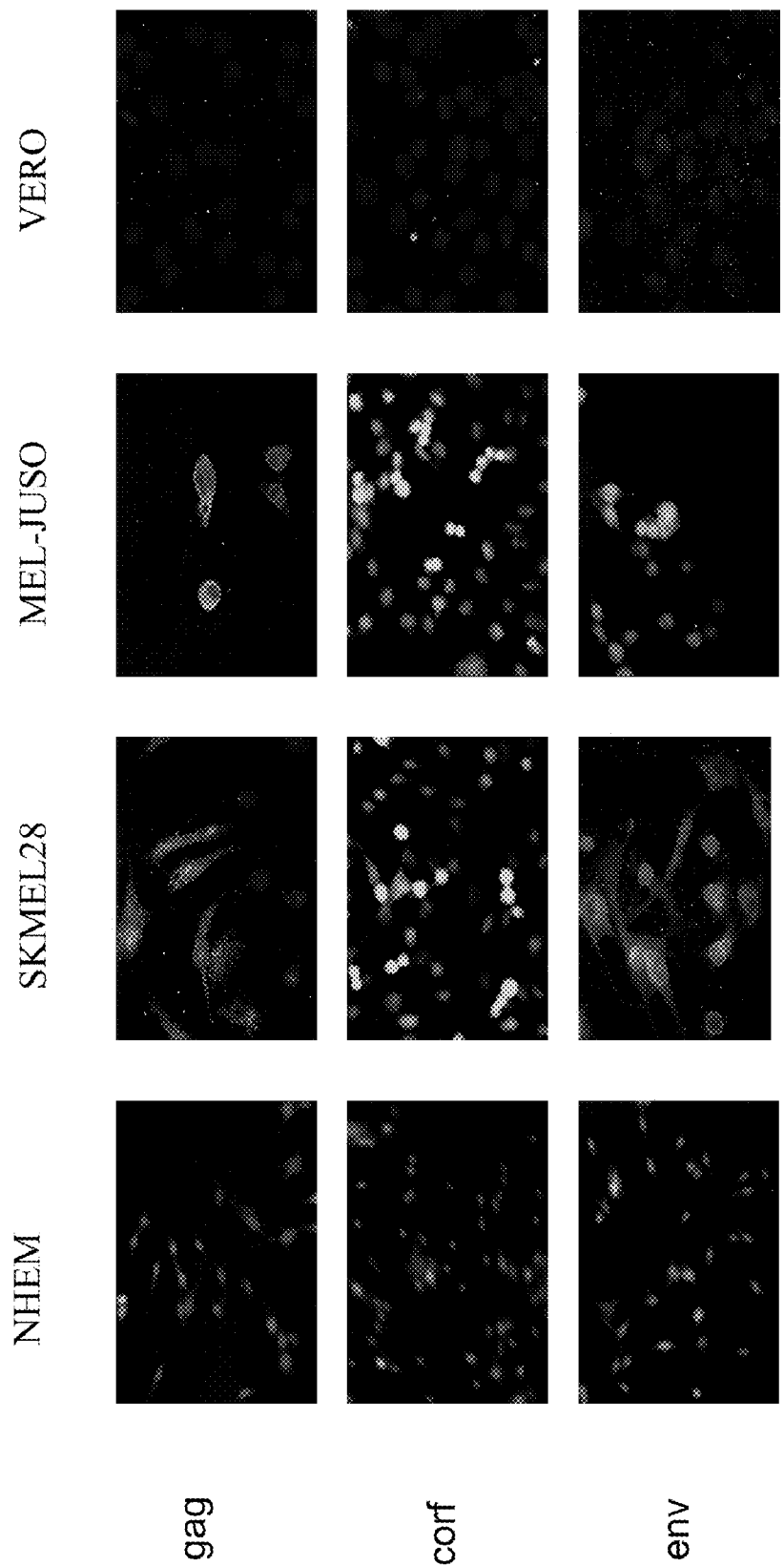
FIGS. 4A and 4B show an immunofluorescence analysis with HERV-K-specific antibodies against gag, cORF, and env.

FIG. 4a shows that the melanoma cell lines Mel-Juso and SK-Mel28 express the gag, cORF and env proteins. The percentage of gag-expressing cells was in the range of 1-10%, cORF was found to be present in about 20%, while expression of the env protein was detected in about 10% of the analyzed cells. Expression of gag and env was found in the cytoplasm, while cORF was mainly found in the nucleus. In contrast, cultured human melanocytes (Nhem) and Vero cells did not react with any HERV-K-specific antisera. None of the corresponding preimmune-sera was reactive with any of the cells tested.

Immunofluorescence analysis was performed with touch preparation of a primary melanoma (first column); touch preparation of a nevus (second column); paraffin preparation primary melanoma (third column); paraffin preparation nevus (fourth column). Retroviral proteins are present in the melanoma preparations but absent from nevus tissue.

Figure 4B:
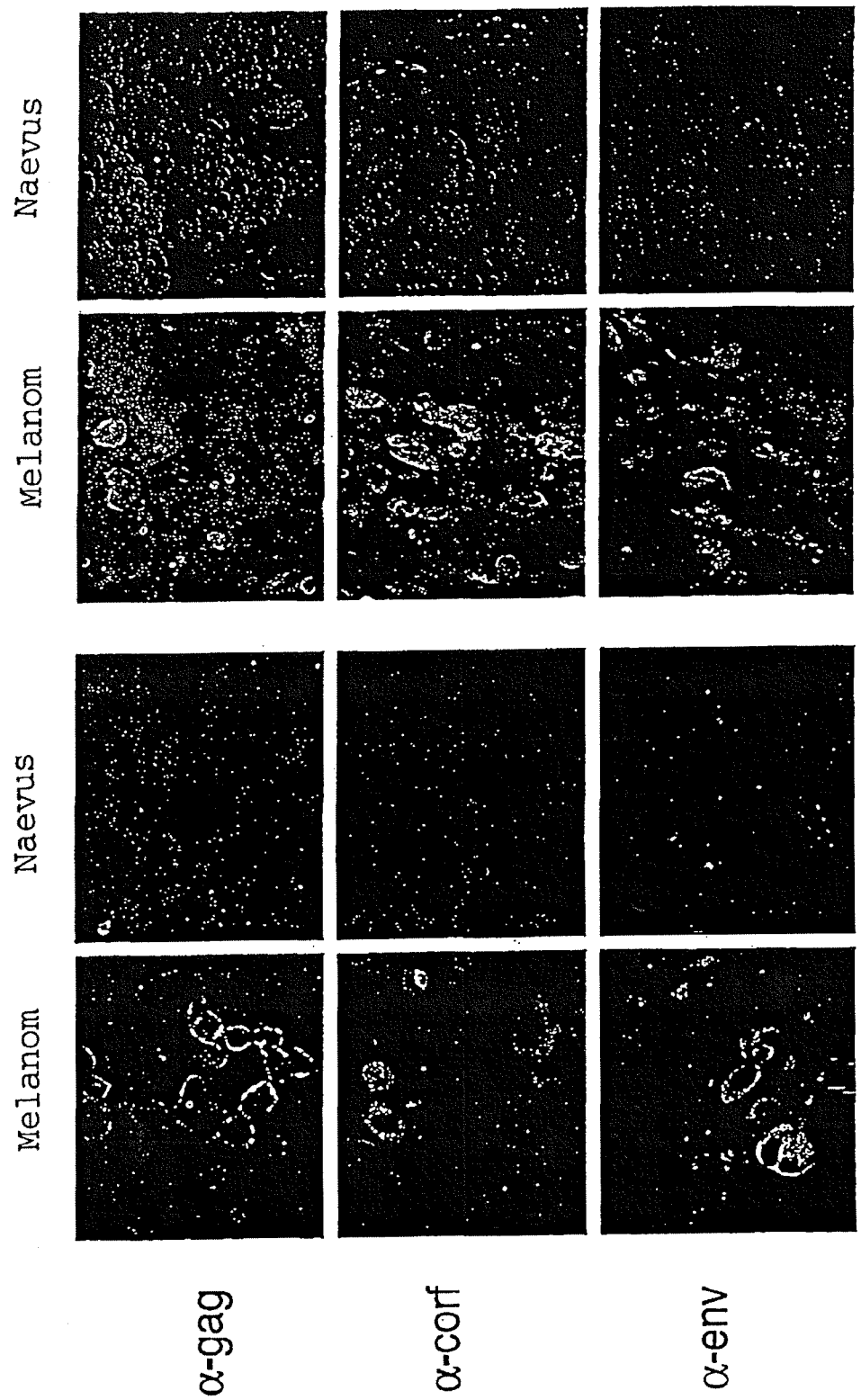

It was then analyzed whether these proteins are also expressed in primary melanoma. FIG. 4b shows that gag, cORF, and env were detected in touch preparations and paraffin sections of a primary melanoma but not in the corresponding preparations of a nevus.

Example 7

Melanoma Cell Derived Particles are Infectious

Supernatants of approximately $10^8$ melanoma cells were loaded on 30% sucrose cushions and centrifuged at 28K. The resulting pellets were washed and resuspended in 500 µl PBS. For infection studies human 293 cells were grown to approximately 30% confluency and exposed overnight to the particle preparations in the presence of 8 µg/ml polybrene. As controls, cells were treated with particle preparations that were heat inactivated 30 min at 60° C. or mock-treated. 293 cells were exposed to particle preparations from the melanoma cell line SKMel28.

Figure 5:
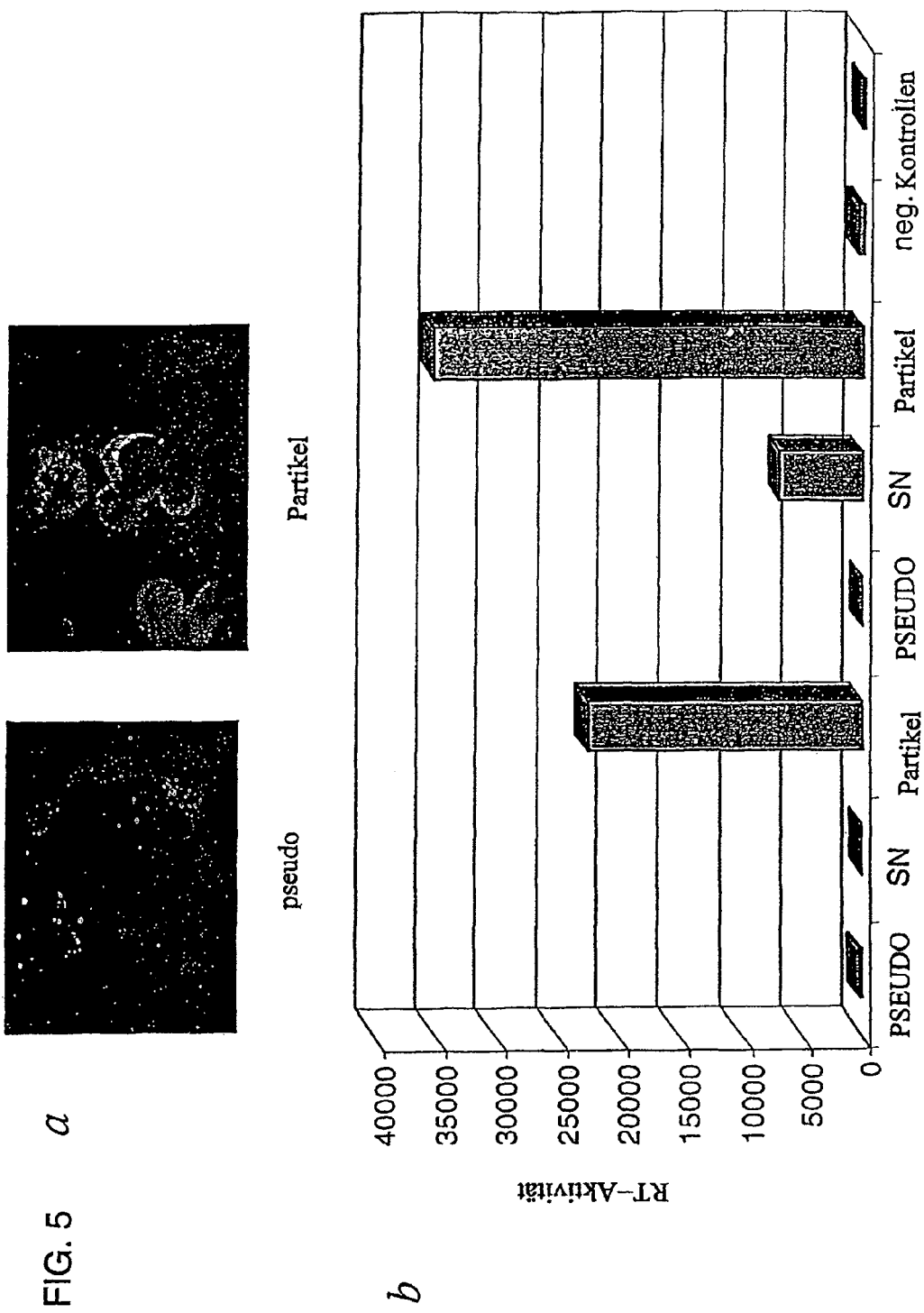
FIG. 5 shows cells infected with melanoma-associated particles.

The human epithelial cell line 293 is a well established target for retrovirus infection. Immunofluorescence with HERV-K specific gag antibodies was performed three weeks post infection (p.i.). Control cells were mock-treated. 293 cells were treated with the melanoma-derived viral particles, and demonstrate that upon treatment they express the HERV-K specific gag-protein (FIG. 5a). Moreover, expression of the retroviral proteins correlated with the level of pelletable RT-activity in the supernatants (FIG. 5b), suggesting that the 293 cells were infected with the melanoma-derived particles. However, due to the high copy numbers of various HERV sequences present in the human genome it was not possible to demonstrate that expression of proteins and production of RT-containing particles was derived from de novo integrated retroviral DNA into the hosts genome. Therefore this question was addressed in bovine MDBK cells.

Example 8

Infection of MDBK Cells

It was tested whether the melanoma-derived particles are infectious. Due to the high copy numbers of various HERV sequences present in the human genome it is difficult to demonstrate in human cells whether virus particles produced are derived from endogenous or exogenous virus. This question was therefore addressed in bovine MDBK cells which are free of viruses that are homologous to HERV-K. MDBK cells were exposed to melanoma derived particle preparations and passaged at a ratio of 1:10. Supernatants of these cells were analyzed by RT-PCR with pol-specific HERV primers as described below:

Cell free supernatants of approximately $10^8$ 518A2 melanoma cells were loaded on 20% sucrose cushions and pelleted at 28K in a Beckmann SW28 rotor. The resulting pellets were washed and resuspended in 500 µl PBS. For infection studies bovine MDBK cells were grown to approximately 30% confluency and exposed overnight to 100 µl aliquots of the particle preparations in the presence of 0.8% polybrene. As controls, cells were treated with particle preparations that were heat inactivated. 24 hour post infection (p.i.) the inoculum was removed, the cells were washed twice with PBS and incubated with normal media. Starting at 7 days p.i. the cells were continuously passaged at a ratio of 1:10 and the supernatants were analyzed for the presence of viral particles by detecting particle-associated RNA. In addition 1.5 ml of the supernatants from infected MDBK cells were put onto new (uninfected) MDBK cells, in the presence of polybrene. 24 hours later the cells were washed twice with PBS and incubated for 7 days, and passaged at a ratio of 1:10. The release of particles from the cells was determined by detecting particle-associated RNA in the supernatants by RT-PCR as described below:

For detecting particles released by the cells, supernatants from approximately $10^7$ 518A2 or infected MDBK cells were filtered, pelleted 2 hours at 28K and resuspended in 500 µl Trizol. To this suspension 100 µl chloroform were added. After vortexing and centrifugation the upper phase was precipitated with isopropanol. The precipitate was pelleted by centrifugation and washed with 70% ethanol. The pellet was resuspended, treated with DNase in the presence of 25 mM $MgCl_2$ for 45 min at 37° C., and the DNAse was inactivated for 10 min at 65° C. After precipitation with 96% ethanol, the pellet was washed with 70% ethanol, resuspended in reverse transcription (RT) reaction buffer and RT was performed with the random primer p(dN)6.1/10 of the reverse transcription reaction was used as template for PCR with the oligonucleotide primers 5'108 propol 3925 5'CCACTGTAGAGCCTC-CTAAACCC 3' (SEQ ID No 6) and 3'108 pol 4315 5' GCTG-GTATAGTAAAGGCAAATTTTTC 3' (SEQ ID No 7) (Codon Genetic Systems, Austria) which correspond to conserved regions within the pol gene.

10 µl of each amplification product were analyzed by electrophoresis in a 1.5% agarose gel and visualized by ethidium bromide staining. An aliquot of the amplification product was cloned and sequenced. Expression of HERV-specific RNA expressed in MDBK cells was detected by RT-PCR of total genomic RNA derived from approximately $10^7$ cells in the same manner.

Figure 6:
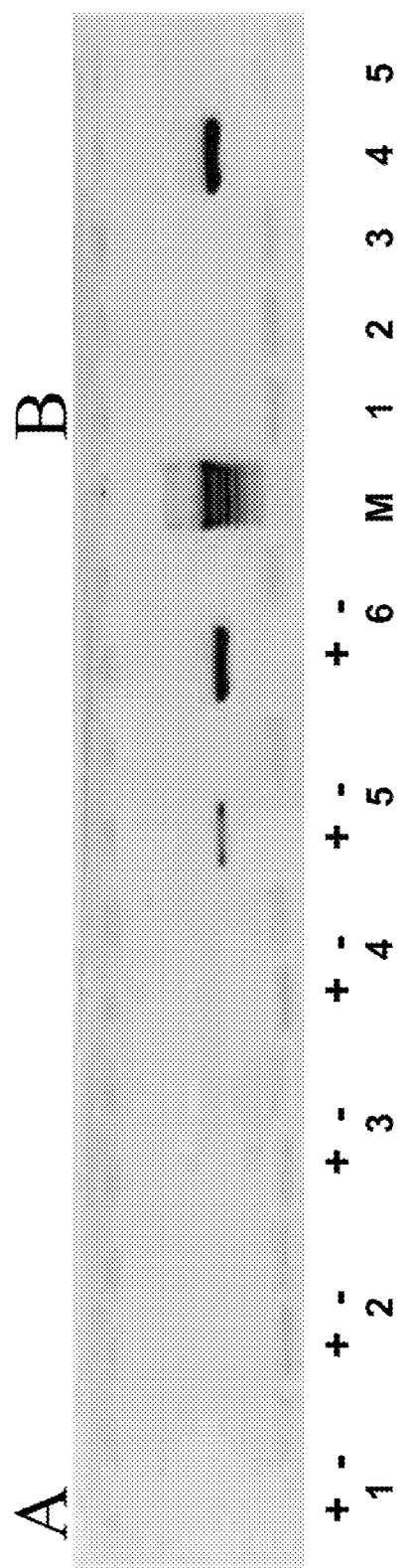
FIG. 6 shows the detection of particle associated RNA and supernatants from infected MDBK cells.

FIG. 6 shows the result after the first passage. Lanes 1-6: After infection cells were passaged 1:10 and supernatants were analyzed by RT-PCR with pol-specific primers (+). Absence of contaminating DNA was analyzed by omitting the RT step (−); Lane 1, no template control; lane 2, heat inactivated particles; lane 3, particle preparation diluted 1:100, lane 4, 1:10 dilution, lane 5, undiluted particle preparations; lane 6, 518A2 supernatant; M, molecular weight marker; Analysis of genomic DNA with pol-specific primers by PCR. Lane 1, no template control; lane 2, no template control; lane 3, MDBK DNA; lane 4, 518A2 DNA, lane 5, no enzyme control. Infection with undiluted particle preparations revealed a pol-specific amplification product (lane 5, +), while infection with particle preparations that were diluted 1:10 (lane 4+), diluted 1:100 (lane 3+) or were heat inactivated (lane 2+) did not. None of the reactions revealed a signal when the RT step was omitted, excluding that the signals were derived from genomic DNAs contaminations (lanes 2-6, −). The presence of particle associated viral sequences in the supernatant of the melanoma-derived particle exposed MDBK cells indicates that melanoma-derived particles are capable to infect bovine cells.

Sequence analysis of the amplification product of lane 5 revealed the nucleotide sequence

```
                                              (SEQ ID No 8)
5'CCACTGTAGAGCCTCCTAAACCCATACCATTAACTTGGAAAACAGAAA

AACCGGTGTGGGTAAATCAGTGGCCGCTACCAAAACAAAAACTGGAGGCT

TTACATTTATTAGCAAATGAACAGTTAGAAAAGGGTCATATTGAGCCTTC

GTTCTCACCTTGGAATTCTCCTGTGTTTGTAATTCAGAAGAAATCAGGCA

AATGGCATATGTTAACTGACTTAAAGGCCGTAAACGCCGTAATTCAACCC

AT 3'.
```

This sequence is highly homologues (98%) to the sequence from HERV-K 108.

Example 9

Supernatants from Infected MDBK Cells Contain Infectious Particles

Cell free supernatants from cells exposed to undiluted melanoma particle preparations were put onto new (uninfected) MDBK cells which were subsequently passaged 3 times at a ratio of 1:10

FIG. 7 shows the transfer of supernatants from melanoma-particle exposed MDBK cells to uninfected MDBK cells. 24 hours later cells were washed twice with PBS, incubated for one week, and subsequently passaged at a ratio of 1:10. FIG. 7a shows pelleted supernatants from these cells which were analyzed for release of particle-associated RNA by RT-PCR with pol-specific primers (lanes 1, 3, 5, 7). As negative controls supernatants from MDBK cells exposed to heat inactivated particles were transferred to MDBK cells which were treated and analyzed in the same manner (lanes 2, 4, 6, 8). Lanes 1 and 2: 5 days after transfer; lanes 3 and 4: passage 1; lanes 5 and 6: passage 2; lanes 7 and 8: passage 3; lane M: molecular weight marker (Boehringer Mannheim VIII); lane 9: negative control: pelleted supernatant from uninfected MDBK cells; lane 10: positive control: pelleted supernatants from 518A2 cells; FIG. 7b shows the expression of HERV-specific RNAs which was analyzed by RT-PCR from whole genomic RNA of MDBK cells from passage 1 with pol-specific primers. Lane 1: MDBK cells treated with supernatants from infected MDBK cells; lane 2: MDBK cells treated with supernatants from MDBK cells exposed to heat inactivated melanoma-derived particle preparations; lane M, molecular weight marker (Boehringer Mannheim VIII); lane 3, negative control: PCR of genomic DNA derived from uninfected MDBK cells; lane 4, positive control: PCR of genomic DNA derived from 518A2 cells; lane 5: non-template control. Lanes 1, 3, 5, and 7 correspond to passages 0, 1, 2, and 3 respectively. Lanes 2, 4, 6, and 8 are the negative controls and correspond to passages 0, 1, 2, and 3 of cells treated with supernatants from cells exposed to heat inactivated particle preparations.

Shown is the presence of particle associated RNA as indicated by the presence of a pol-specific sequences. Pol-specific signals were detectable after passages 0, 1, and 3, suggesting the presence of viral particles (lanes 1, 3, and 7). Analysis of passage number 2 did not reveal a pol-signal which might be due to fluctuating production levels of viral particles (lane 5). Transfer of supernatants from MDBK cells that were treated with heat inactivated particle preparations did not result in the release of particles (lanes 2, 4, 6, and 8). PCR alone did not reveal pol-specific signals, indicating that the signals obtained by RT-PCR are derived from RNA. The result that transfer of the supernatant from infected MDBK cells to uninfected MDBK cells resulted in the release of particle associated viral RNA, indicates that infection with melanoma derived particles of MDBK cells is productive.

These data show that retroviral sequences and infectious particles are expressed in melanoma cells.

Partial sequence analysis, immunoblotting and immuno-electron microscopy studies show the particles belong to the HERV-K family. In contrast to other known HERV-K like viruses, which lack infectivity, the env precursor appears to be cleaved in the melanoma derived particles, resulting in approximately equimolar amounts of the precursor and the putative transmembrane domain. Cell-free particle preparations from the melanoma cells were able to infect both human and bovine cells, as indicated by the appearance of the viral proteins gag, cORF, and env, and pelletable RT-activity in the supernatants of infected cells. Moreover, the fact that human pol and gag sequences in the genome of the infected bovine MDBK cells were detected, indicates that the melanoma-associated viruses are capable of de novo integration of their genome. This observation also suggests the presence of a functional integrase in the viral particles.

Figure 8A:
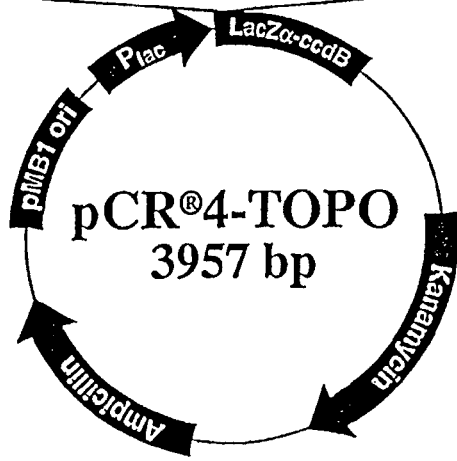

FIG. 8a shows the pCR4-Topo vector into which the MERV gag, pro, pol and env sequences isolated from the above described infected bovine cells were inserted. The primers used in the above examples are shown in the boxes of each sequence of vectors shown in FIG. 8b. These vectors were deposited on 26 Sep. 2001 at the DSMZ under the names MERV-env, MERV-gag, MERV-prt and MERV-pol according to the Budapest Treaty.

The invention claimed is:

1. An isolated polynucleotide molecule comprising a nucleotide sequence of an infectious human endogenous retrovirus, which sequence is or is complementary to a sequence which:
   (a) has at least 99% identity to the full length of SEQ ID NO:1;
   (b) has 100% identity to a fragment of SEQ ID NO:1, the fragment comprising at least 15 contiguous nucleotides of SEQ ID NO:1 and including at least one of nucleotides 416, 602, 630, 639, 654, 738, 799, 802, 866, 945, 953, 972, 1149, 1348, 1413, 1642, 1653, 1668, 1701, 1989, 2068, 2087, 2090, 2097, 2100, 2124, 2163, 2198, 2238, 2253, 2273, 2305, 2313, 2330, 2461, 2808, 2815, 2816, 2878, 2938, 2974, 3052, 3091, 3105, 3124, 3178, 3363, 5402, 5719, 6456, 6458, 6464, 6802, 7146, 7262, 7340, 7347, 7388, or 7436 of SEQ ID NO:1; and/or
   (c) comprises the sequence inserted into a vector pCR4-Topo and deposited as any of "MERV-env", "MERV-gag", "MERV-prt" and "MERV-pol" at the DSMZ on 26 Sep. 2001.

2. The polynucleotide molecule of claim 1, comprising the sequence of SEQ ID NO:1.

3. The polynucleotide molecule of claim 1, wherein the fragment of SEQ ID NO:1 comprises a sequence identical to the full-length of SEQ ID NO:2, SEQ ID NO:3, SEQ ID NO:4, or SEQ ID NO:5.

4. The polynucleotide molecule of claim 1, further defined as encoding an env protein of an infectious human endogenous retrovirus, said polynucleotide molecule comprising a sequence:
   (a) with at least 99.5% identity to the full length of the sequence of SEQ ID NO:2;
   (b) which is complementary to the full length of the nucleotide sequence of said SEQ ID NO:2; and/or (c) comprises the sequence inserted into a vector pCR4-Topo and deposited as "MERV-env".

5. The polynucleotide molecule of claim 1, further defined as encoding a gag protein of an infectious human endogenous retrovirus, said polynucleotide molecule comprising a sequence:
(a) with at least 99.5% identity to the full length of the sequence of SEQ ID NO:4;
(b) which is complementary to the full length of the nucleotide sequence of said SEQ ID NO:4; and/or
(c) comprises the sequence inserted into a vector pCR4-Topo and deposited as "MERV-gag".

6. The polynucleotide molecule of claim 1, further defined as encoding a pro protein of an infectious human endogenous retrovirus, said polynucleotide molecule comprising a sequence:
(a) with at least 98% identity to the full length of the sequence of SEQ ID NO:5;
(b) which is complementary to the full length of the nucleotide sequence of said SEQ ID NO:5; and/or
(c) comprises the sequence inserted into a vector pCR4-Topo and deposited as "MERV-prt".

7. The polynucleotide molecule of claim 1, further defined as encoding a pol protein of an infectious human endogenous retrovirus, said polynucleotide molecule comprising a sequence:
(a) with at least 99% identity to the full length of the sequence of SEQ ID NO:3;
(b) which is complementary to the full length of the nucleotide sequence of said SEQ ID NO:3; and/or
(c) comprises the sequence inserted into a vector pCR4-Topo and deposited as "MERV-pol".

8. The polynucleotide molecule of claim 1, further comprising a detectable label.

9. The polynucleotide molecule of claim 1, further defined as a primer adapted to specifically hybridize to a second polynucleotide molecule of claim 1 in an amplification reaction.

10. The polynucleotide molecule of claim 1, wherein the polynucleotide molecule is comprised in a biologically functional vector.

11. The polynucleotide molecule of claim 10, wherein the biologically functional vector is in inverse orientation with respect to the promoter.

12. The polynucleotide molecule of claim 1, wherein the polynucleotide molecule is comprised in a recombinant host cell.

13. The polynucleotide molecule of claim 12, wherein the host cell is a mammalian cell.

* * * * *

SEQUENCE LISTING

<160> NUMBER OF SEQ ID NOS: 59

<210> SEQ ID NO 1
<211> LENGTH: 7475
<212> TYPE: DNA
<213> ORGANISM: Human endogenous retrovirus

<400> SEQUENCE: 1

```
gctagggtga taatggggca aactaaaagt aaaattaaaa gtaaatatgc ctcttatctc      60
agctttatta aaattctttt aaaaagaggg ggagttaaag tatctacaaa aaatctaatc     120
aagctatttc aaataataga acaatttgc ccatggtttc cagaacaagg aactttagat     180
ctaaaagatt ggaaaagaat tggtaaggaa ctaaacaag caggtaggaa gggtaatatc     240
attccactta cagtatggaa tgattgggcc attattaaag cagctttaga accatttcaa     300
acagaagaag atagcgtttc agtttctgat gccctggaa gctgtataat agattgtaat     360
gaaaacacaa ggaaaaaatc ccagaaagaa acggaaggtt tacattgcga atatgcagca     420
gagccggtaa tggctcagtc aacgcaaaat gttgactata tcaattaca ggaggtgata     480 tatcctgaaa cgttaaaatt agaaggaaaa ggtccagaat tagtggggcc atcagagtct     540
aaaccacgag gcacaagtcc tcttccagca ggtcaggtgc ctgtaacatt acaacctcaa     600
acgcaggtta aagaaaataa gacccaacca ccagtagctt atcaatactg gccgccggct     660
```

```
gaacttcagt atcggccacc cccagaaagt cagtatggat atccaggaat gcccccagca    720
ccacagggca gggcgccgta ccctcagccg cccactagga gacttaatcc tacggcacca    780
cctagtagac agggtagtga actacatgaa attattgata aatcaagaaa ggaaggagat    840
actgaggcat ggcaattccc agtaatgtta gaaccgatgc cacctggaga aggagcccaa    900
gagggagagc ctcccacagt tgaggccaga tacaagtctt tttcaataaa aatgctaaaa    960
gatatgaaag aaggagtaaa acagtatgga cccaactccc cttatatgag acattatta   1020 gattccattg ctcatggaca tagactcatt ccttatgatt gggagattct ggcaaaatcg   1080
tctctctcac cctctcaatt tttacaattt aagacttggt ggattgatgg ggtacaagaa   1140
caggtccaaa gaaatagggc tgccaatcct ccagttaaca tagatgcaga tcaactatta   1200 ggataggtc aaaattggag tactattagt caacaagcat taatgcaaaa tgaggccatt    1260
gagcaagtta gagctatctg ccttagagcc tgggaaaaaa tccaagaccc aggaagtacc   1320
tgcccctcat ttaatacagt aagacaaagt tcaaaagagc cctatcctga ttttgtggca   1380
aggctccaag atgttgctca aaagtcaatt gccgatgaaa aagcccgtaa ggtcatagtg   1440
gagttgatgg catatgaaaa cgccaatcct gagtgtcaat cagccattaa gccattaaaa   1500
ggaaaggttc ctgcaggatc agatgtaatc tcagaatatg taaaagcctg tgatggaatc   1560
ggaggagcta tgcataaagc tatgcttatg gctcaagcaa taacaggagt tgttttagga   1620
ggacaagtta gaacatttgg aggaaaatgt tacaattgtg gtcaaatcgg tcacttaaaa   1680
aagaattgcc cagtcttaaa caaacagaat ataactattc aagcaactac aacaggtaga   1740
gagccacctg acttatgtcc aagatgtaaa aaggaaaac attgggctag tcaatgtcgt    1800
tctaaatttg ataaaaatgg gcaaccattg tcgggaaacg agcaaagggg ccagcctcag   1860
gccccacaac aaactggggc attcccaatt cagccatttg ttcctcaggg ttttcaggga   1920
caacaacccc cactgtccca agtgtttcag ggaataagcc agttaccaca atacaacaat   1980 tgtccccac cacaagcggc agtgcagcag tagatttatg tactatacaa gcagtctctc     2040
tgcttccagg ggagccccca caaaaaatcc ccacagggggt atatggccca ctgcctgaga   2100
ggactgtagg actaatcttg ggaagatcaa gtctaaatct aaaaggagtt caaattcata   2160
ctggtgtggt tgattcagac tataaaggcg aaattcagtt ggttattagc tcttcaattc   2220
cttggagtgc cagtccagga gacaggattg ctgaattatt actcctgcca tatattaagg   2280
gtggaaatag tgaaataaaa agaacaggag ggtttggaag cactgatccg acaggaaagg   2340
ctgcatattg ggcaagtcag gtctcagaga acagacctgt gtgtaaggcc attattcaag   2400
gaaaacagtt tgaagggttg gtagacactg gagcagatgt ctctatcatt gctttaaatc   2460
ggtggccaaa aaattggcct aaccaaaagg ctgttacagg acttgtcggc ataggcacag   2520
cctcagaagt gtatcaaagt acggagattt tacattgctt agggccagat aatcaagaaa   2580
gtactgttca gccaatgatt acttcaattc ctcttaatct gtgggtcga gatttattac   2640 aacaatgggg tgcggaaatc accatgcccg ctccatcata tagccccacg agtcaaaaaa   2700
tcatgaccaa gatgggatat ataccaggaa agggactagg gaaaaatgaa gatggcatta   2760
aaattccagt tgaggctaaa ataaatcaag aaagagaagg aataggtgtat ccttttttagg    2820 ggcggccact gtagagcctc ctaaacccat accattaact tggaaaacag aaaaaccggt   2880
gtgggtaaat cagtggccgc taccaaaaca aaaactggag gctttacatt tattagcgaa   2940
tgaacagtta gaaagggtc atattgagcc ttcattctca ccttggaatt ctcctgtgtt   3000
tgtaattcag aagaaatcag gcaaatggcg tatgttaact gacttaaggg ccgtaaacgc   3060
```

```
cgtaattcaa cccatggggc ctctccaacc tgggttgccc tctctggcca tgatcccaaa    3120
agactggcct ttaattataa ttgatctaaa ggattgcttt tttaccatcc ctctggcgga    3180
gcaggattgc gaaaaatttg cctttactat accagccata ataataaag aaccagccac     3240
caggtttcag tggaaagtgt tacctcaggg aatgcttaat agtccaacta tttgtcagac    3300
ttttgtaggt cgagctcttc aaccagttag agaaagtttt tcagactgtt atattattca    3360
ttatattgat gatattttat gtgctgcaga acgaaagat aaattaattg actgttatac     3420
atttctgcaa gcagaggttg ccaatgctgg actggcaata gcatctgata agatccaaac    3480
ctctactcct tttcattatt tagggatgca gatagaaaat agaaaaatta agccacaaaa    3540
aatagaaata agaaaagaca cattaaaaac actaaatgat tttcaaaaat tactaggaga    3600
tattaattgg attcggccaa ctctaggcat tcctacttat gccatgtcaa atttgttctc    3660
tatcttaaga ggagactcag acttaaatag taaaagaatg ttaaccccag aggcaacaaa    3720
agaaattaaa ttagtggaag aaaaaattca gtcagcgcaa ataaatagaa tagatccctt    3780
agccccactc caacttttga ttttttgccac tgcacattct ccaacaggca tcattattca    3840
aaatactgat cttgtggagt ggtcattcct tcctcacagt acagttaaga cttttacatt    3900
gtacttggat caaatagcta cattaatcgg tcagacaaga ttacgaataa taaaattatg    3960
tgggaatgac ccagacaaaa tagttgtccc tttaaccaag gaacaagtta gacaagcctt    4020
tatcaattct ggtgcatgga agattggtct tgctaatttt gtgggaatta ttgataatca    4080
ttacccaaaa acaagatctt tccagttctt aaaattgact acttggattc tacctaaaat    4140
taccagacgt gaacctttag aaaatgctct aacagtattt actgatggtt ccagcaatgg    4200
aaaagcagct tacacaggac cgaaagaacg agtaatcaaa actccatatc aatcggctca    4260
aagagcagag ttggttgcag tcattacagt gttacaagat tttgaccaac ctatcaatat    4320
tatatcagat tctgcatatg tagtacaggc tacaagggat gttgagacag ctctaattaa    4380
atatagcatg gatgatcagt taaaccagct attcaattta ttacaacaaa ctgtaagaaa    4440
aagaaatttc ccatttata ttacacatat tcgagcacac actaatttac cagggccttt      4500
gactaaagca aatgaacaag ctgacttact ggtatcatct gcactcataa aagcacaaga    4560
acttcatgct ttgactcatg taaatgcagc aggattaaaa aacaaatttg atgtcacatg    4620
gaaacaggca aaagatattg tacaacattg cacccagtgt caagtcttac acctgcccac    4680
tcaagaggca ggagttaatc ccagaggtct gtgtcctaat gcattatggc aaatggatgt    4740
cacgcatgta ccttcatttg gaagattatc atatgttcac gtaacagttg atacttattc    4800
acatttcata tgggcaactt gccaaacagg agaaagtact tcccatgtta aaaaacattt    4860
attgtcttgt tttgctgtaa tgggagttcc agaaaaaatc aaaactgaca atggaccagg    4920
atattgtagt aaagctttcc aaaaattctt aagtcagtgg aaatttcac atacaacagg     4980
aattccttat aattcccaag acaggccat agttgaaaga actaatagaa cactcaaaac     5040
tcaattagtt aaacaaaaag aagggggaga cagtaaggag tgtaccactc ctcagatgca    5100
acttaatcta gcactctata ctttaaattt tttaaacatt tatagaaatc agactactac    5160
ttctgcagaa caacatctta ctggtaaaaa gaacagccca catgaaggaa aactaatttg    5220
gtggaaagat aataaaaata agacatggga aatagggaag gtgataacgt ggggagagg     5280
ttttgcttgt gtttcaccag gagaaaatca gcttcctgtt tggataccca ctagacattt    5340
gaagttctac aatgaaccca tcagagatgc aaagaaaagc acctccgcgg agacggagac    5400
accgcaatcg agcaccgttg actcacaaga tgaacaaaat ggtgacgtca gaagaacaga    5460
```

```
tgaagttgcc atccaccaag aaggcagagc cgccaacttg ggcacaacta agaagctga      5520 cgcagttagc tacaaaatat ctagagaaca caaaggtgac acaaacccca gagagtatgc    5580
tgcttgcagc cttgatgatt gtatcaatgg tggtaagtct ccctatgcct gcaggagcag    5640
ctgcagctaa ctatacctac tgggcctatg tgcctttccc gcccttaatt cgggcagtca    5700
catggatgga taatcctata gaagtatatg ttaatgatag tgtatgggta cctggcccca    5760
tagatgatcg ctgccctgcc aaacctgagg aagaagggat gatgataaat atttccattg    5820
ggtatcatta tcctcctatt tgcctaggga gagcaccagg atgtttaatg cctgcagtcc    5880
aaaattggtt ggtagaagta cctactgtca gtcccatctg tagattcact tatcacatgg    5940
taagcgggat gtcactcagg ccacgggtaa attatttaca agactttttct tatcaaagat    6000 cattaaaatt tagacctaaa gggaaacctt gccccaagga aattcccaaa gaatcaaaaa    6060
atacagaagt tttagtttgg aagaatgtg tggccaatag tgcggtgata ttacaaaaca    6120
atgaattcgg aactattata gattgggcac ctcgaggtca attctaccac aattgctcag    6180
gacaaactca gtcgtgtcca agtgcacaag tgagtccagc tgttgatagc gacttaacag    6240
aaagtttaga caaacataag cataaaaaat tgcagtcttt ctacccttgg aatggggag    6300 aaaaaggaat ctctaccca agaccaaaaa tagtaagtcc tgtttctggt cctgaacatc    6360
cagaattatg gaggcttact gtggcctcac accacattag aatttggtct ggaaatcaaa    6420
ctttagaaac aagagatcgt aagccatttt atactgtcga cctaaattcc agtctaacag    6480
ttcctttaca aagttgcgta aagccccctt atatgctagt tgtaggaaat atagttatta    6540
aaccagactc ccagactata acctgtgaaa attgtagatt gcttacttgc attgattcaa    6600
cttttaattg gcaacaccgt attctgctgg tgagagcaag agagggcgtg tggatccctg    6660
tgtccatgga ccgaccgtgg gaggcctcgc catccgtcca tattttgact gaagtattaa    6720
aaggtgtttt aaatagatcc aaaagattca ttttttacttt aattgcagtg attatgggat    6780
taattgcagt cacagctacg ggtgctgtag caggagttgc attgcactct tctgttcagt    6840
cagtaaactt tgttaatgat tggcaaaaaa attctacaag attgtggaat tcacaatcta    6900
gtattgatca aaaattggca aatcaaatta atgatcttag acaaactgtc atttggatgg    6960
gagacagact catgagctta gaacatcgtt tccagttaca atgtgactgg aatacgtcag    7020 attttttgtat tacaccccaa atttataatg agtctgagca tcactgggac atggttagac    7080
gccatctaca gggaagagaa gataatctca ctttagacat ttccaaatta aaagaacaaa    7140 tttttcaaagc atcaaaagcc catttaaatt tggtgccagg aactgaggca attgcaggag    7200
ttgctgatgg cctcgcaaat cttaaccctg tcacttgggt taagaccatt ggaagtacta    7260
caattataaa tctcatatta atccttgtgt gcctgttttg tctgttgtta gtctgcaggt    7320
gtacccaaca gctccgaagg gacagcaacc atcgagaacg ggccatgatg acgatggcgg    7380
ttttgtcaaa aagaaaaggg ggaaatgtgg ggaaagcaa gagagatcag attgtcactg    7440
tgtctgtgta gaaagaagta gacataggag actcc                              7475
```

<210> SEQ ID NO 2
<211> LENGTH: 2129
<212> TYPE: DNA
<213> ORGANISM: Human endogenous retrovirus

<400> SEQUENCE: 2

```
ctacaatgaa cccatcagag atgcaaagaa aagcacctcc gcggagacgg agacaccgca      60
atcgagcacc gttgactcac aagatgaaca aaatggtgac gtcagaagaa cagatgaagt     120
```

-continued

```
tgccatccac caagaaggca gagccgccaa cttgggcaca actaaagaag ctgacgcagt      180
tagctacaaa atatctagag aacacaaagg tgacacaaac cccagagagt atgctgcttg      240
cagccttgat gattgtatca atggtggtaa gtctccctat gcctgcagga gcagctgcag      300
ctaactatac ctactgggcc tatgtgcctt cccgccctt aattcgggca gtcacatgga       360
tggataatcc tatagaagta tatgttaatg atagtgtatg ggtacctggc cccatagatg      420
atcgctgccc tgccaaacct gaggaagaag ggatgatgat aaatatttcc attgggtatc      480
attatcctcc tatttgccta gggagagcac caggatgttt aatgcctgca gtccaaaatt      540
ggttggtaga agtacctact gtcagtccca tctgtagatt cacttatcac atggtaagcg      600
ggatgtcact caggccacgg gtaaattatt tacaagactt ttcttatcaa agatcattaa      660
aatttagacc taaagggaaa ccttgcccca aggaaattcc caagaatca aaaaatacag       720 aagttttagt ttgggaagaa tgtgtggcca atagtgcggt gatattacaa acaatgaat       780 tcggaactat tatagattgg gcacctcgag gtcaattcta ccacaattgc tcaggacaaa      840
ctcagtcgtg tccaagtgca caagtgagtc cagctgttga tagcgactta acagaaagtt      900
tagacaaaca taagcataaa aaattgcagt cttctaccc ttgggaatgg ggagaaaaag       960
gaatctctac cccaagacca aaatagtaa gtcctgtttc tggtcctgaa catccagaat      1020
tatggaggct tactgtggcc tcacaccaca ttagaatttg gtctggaaat caaactttag     1080
aaacaagaga tcgtaagcca ttttatactg tcgacctaaa ttccagtcta acagttcctt     1140 tacaagttg cgtaaagccc ccttatatgc tagttgtagg aaatatagtt attaaaccag      1200
actcccagac tataaccttg gaaaattgta gattgcttac ttgcattgat tcaactttta     1260
attggcaaca ccgtattctg ctggtgagag caagagaggg cgtgtggatc cctgtgtcca     1320
tggaccgacc gtgggaggcc tcgccatccg tccatatttt gactgaagta ttaaaaggtg     1380
ttttaaatag atccaaaaga ttcatttta ctttaattgc agtgattatg ggattaattg      1440
cagtcacagc tacgggtgct gtagcaggag ttgcattgca ctcttctgtt cagtcagtaa     1500
actttgttaa tgattggcaa aaaaattcta caagattgtg gaattcacaa tctagtattg     1560
atcaaaaatt ggcaaatcaa attaatgatc ttagacaaac tgtcatttgg atgggagaca     1620
gactcatgag cttagaacat cgtttccagt tacaatgtga ctggaatacg tcagattttt     1680
gtattacacc ccaaatttat aatgagtctg agcatcactg gacatggtt agacgccatc      1740 tacagggaag agaagataat ctcactttag acatttccaa attaaagaa caaattttca      1800 aagcatcaaa agcccattta aatttggtgc aggaactga gcaattgca ggagttgctg       1860 atggcctcgc aaatcttaac cctgtcactt gggttaagac cattggaagt actacaatta     1920
taaatctcat attaatcctt gtgtgcctgt tttgtctgtt gttagtctgc aggtgtaccc     1980
aacagctctg aagggacagc aaccatcgag aacgggccat gatgacgatg gcggttttgt     2040
caaaaagaaa aggggggaaat gtggggaaaa gcaagagaga tcagattgtc actgtgtctg     2100
tgtagaaaga agtagacata ggagactcc                                        2129
```

<210> SEQ ID NO 3
<211> LENGTH: 2180
<212> TYPE: DNA
<213> ORGANISM: Human endogenous retrovirus

<400> SEQUENCE: 3

```
gaaaaatttg cctttactat accagccata aataataaag aaccagccac caggtttcag       60
tggaaagtgt tacctcaggg aatgcttaat agtccaacta tttgtcagac ttttgtaggt      120
```

```
cgagctcttc aaccagttag agaaaagttt tcagactgtt atattattca ttatattgat    180
gatattttat gtgctgcaga aacgaaagat aaattaattg actgttatac atttctgcaa    240
gcagaggttg ccaatgctgg actggcaata gcatctgata agatccaaac ctctactcct    300
tttcattatt tagggatgca gatagaaaat agaaaaatta agccacaaaa aatagaaata    360
agaaaagaca cattaaaaac actaaatgat tttcaaaaat tactaggaga tattaattgg    420
attcggccaa ctctaggcat tcctactat gccatgtcaa atttgttctc tatcttaaga    480
ggagactcag acttaaatag taaaagaatg ttaaccccag aggcaacaaa agaaattaaa    540
ttagtggaag aaaaaattca gtcagcgcaa ataaatagaa tagatccctt agccccactc    600
caacttttga ttttgccac tgcacattct ccaacaggca tcattattca aaatactgat    660
cttgtggagt ggtcattcct tcctcacagt acagttaaga cttttacatt gtacttggat    720
caaatagcta cattaatcgg tcagacaaga ttacgaataa taaaattatg tgggaatgac    780
ccagacaaaa tagttgtccc tttaaccaag gaacaagtta gacaagcctt tatcaattct    840
ggtgcatgga agattggtct tgctaatttt gtgggaatta ttgataatca ttacccaaaa    900
acaaagatct tccagttctt aaaattgact acttggattc tacctaaaat taccagacgt    960
gaacctttag aaaatgctct aacagtattt actgatggtt ccagcaatgg aaaagcagct   1020
tacacaggac cgaaagaacg agtaatcaaa actccatatc aatcggctca agagcagag    1080 ttggttgcag tcattacagt gttacaagat tttgaccaac ctatcaatat tatatcagat   1140
tctgcatatg tagtacaggc tacaagggat gttgagacag ctctaattaa atatagcatg   1200
gatgatcagt taaccagct attcaattta ttacaacaaa ctgtaagaaa aagaaatttc    1260
ccattttata ttcacatat tcgagcacac actaatttac cagggccttt gactaaagca    1320
aatgaacaag ctgacttact ggtatcatct gcactcataa aagcacaaga acttcatgct   1380
ttgactcatg taaatgcagc aggattaaaa aacaaatttg atgtcacatg gaaacaggca   1440
aaagatattg tacaacattg cacccagtgt caagtcttac acctgccccac tcaagaggca   1500 ggagttaatc ccagaggtct gtgtcctaat gcattatggc aaatggatgt cacgcatgta   1560
ccttcatttg gaagattatc atatgttcac gtaacagttg atacttattc acatttcata   1620
tgggcaactt gccaaacagg agaaagtact tcccatgtta aaaaacattt attgtcttgt   1680
tttgctgtaa tgggagttcc agaaaaaatc aaaactgaca atggaccagg atattgtagt   1740 aaagcttttcc aaaaattctt aagtcagtgg aaaatttcac atacaacagg aattccttat   1800
aattcccaag acaggccat agttgaaaga actaatagaa cactcaaaac tcaattagtt   1860
aaacaaaaag aagggggaga cagtaaggag tgtaccactc ctcagatgca acttaatcta   1920
gcactctata ctttaaattt tttaaacatt tatagaaatc agactactac ttctgcagaa   1980
caacatctta ctggtaaaaa gaacagccca catgaaggaa aactaatttg gtggaaagat   2040
aataaaaata agacatggga aatagggaag gtgataacgt gggggagagg ttttgcttgt   2100
gtttcaccag gagaaaatca gcttcctgtt tggataccca ctagacattt gaagttctac   2160
aatgaaccca tcagagatgc                                               2180
```

<210> SEQ ID NO 4
<211> LENGTH: 2013
<212> TYPE: DNA
<213> ORGANISM: Human endogenous retrovirus

<400> SEQUENCE: 4

```
gctagggtga taatggggca aactaaaagt aaaattaaaa gtaaatatgc ctcttatctc     60
```

```
agctttatta aaattctttt aaaaagaggg ggagttaaag tatctacaaa aaatctaatc    120
aagctatttc aaataataga acaattttgc ccatggtttc cagaacaagg aactttagat    180
ctaaaagatt ggaaaagaat tggtaaggaa ctaaacaag caggtaggaa gggtaatatc     240
attccactta cagtatggaa tgattgggcc attattaaag cagctttaga accatttcaa    300
acagaagaag atagcgtttc agtttctgat gcccctggaa gctgtataat agattgtaat    360
gaaaacacaa ggaaaaaatc ccagaaagaa acggaaggtt acattgcga atatgcagca    420 gagccggtaa tggctcagtc aacgcaaaat gttgactata atcaattaca ggaggtgata    480
tatcctgaaa cgttaaaatt agaaggaaaa ggtccagaat tagtggggcc atcagagtct    540
aaaccacgag gcacaagtcc tcttccagca ggtcaggtgc ctgtaacatt acaacctcaa    600
acgcaggtta aagaaaataa gacccaacca ccagtagctt atcaatactg gccgccggct    660
gaacttcagt atcggccacc cccagaaagt cagtatggat atccaggaat gcccccagca    720
ccacagggca gggcgccgta ccctcagccg cccactagga gacttaatcc tacggcacca    780
cctagtagac agggtagtga actacatgaa attattgata aatcaagaaa ggaaggagat    840
actgaggcat ggcaattccc agtaatgtta gaaccgatgc cacctggaga aggagcccaa    900
gagggagagc ctcccacagt tgaggccaga tacaagtctt tttcaataaa aatgctaaaa    960
gatatgaaag aaggagtaaa acagtatgga cccaactccc cttatatgag gacattatta   1020
gattccattg ctcatggaca tagactcatt ccttatgatt gggagattct ggcaaaatcg   1080
tctctctcac cctctcaatt tttacaattt aagacttggt ggattgatgg ggtacaagaa   1140
caggtccaaa gaaatagggc tgccaatcct ccagttaaca tagatgcaga tcaactatta   1200
ggaataggtc aaaattggag tactattagt caacaagcat taatgcaaaa tgaggccatt   1260
gagcaagtta gagctatctg ccttagagcc tgggaaaaaa tccaagaccc aggaagtacc   1320
tgcccctcat ttaatacagt aagacaaagt tcaaaagagc cctatcctga ttttgtggca   1380
aggctccaag atgttgctca aaagtcaatt gccgatgaaa aagcccgtaa ggtcatagtg   1440
gagttgatgg catatgaaaa cgccaatcct gagtgtcaat cagccattaa gccattaaaa   1500
ggaaaggttc ctgcaggatc agatgtaatc tcagaatatg taaaagcctg tgatggaatc   1560
ggaggagcta tgcataaagc tatgcttatg gctcaagcaa taacaggagt tgttttagga   1620
ggacaagtta gaacatttgg aggaaaatgt acaattgtg gtcaaatcgg tcacttaaaa   1680
aagaattgcc cagtcttaaa caaacagaat ataactattc aagcaactac aacaggtaga   1740
gagccacctg acttatgtcc aagatgtaaa aaaggaaaac attgggctag tcaatgtcgt   1800
tctaaatttg ataaaaatgg gcaaccattg tcgggaaacg agcaaagggg ccagcctcag   1860
gccccacaac aaactggggc attcccaatt cagccatttg ttcctcaggg ttttcaggga   1920
caacaacccc cactgtccca agtgtttcag ggaataagcc agttaccaca atacaacaat   1980
tgtcccccac acaagcggc agtgcagcag tag                                  2013
```

<210> SEQ ID NO 5
<211> LENGTH: 1224
<212> TYPE: DNA
<213> ORGANISM: Human endogenous retrovirus

<400> SEQUENCE: 5

```
caagcggcag tgcagcagta gatttatgta ctatacaagc agtctctctg cttccagggg    60
agcccccaca aaaatcccc acaggggtat atggcccact gcctgagagg actgtaggac    120
taatcttggg aagatcaagt ctaaatctaa aaggagttca aattcatact ggtgtggttg    180
```

```
attcagacta taaaggcgaa attcagttgg ttattagctc ttcaattcct tggagtgcca     240
gtccaggaga caggattgct gaattattac tcctgccata tattaagggt ggaaatagtg     300
aaataaaaag aacaggaggg tttggaagca ctgatccgac aggaaaggct gcatattggg     360
caagtcaggt ctcagagaac agacctgtgt gtaaggccat tattcaagga aaacagtttg     420
aagggttggt agacactgga gcagatgtct ctatcattgc tttaaatcgg tggccaaaaa     480
attggcctaa ccaaaaggct gttacaggac ttgtcggcat aggcacagcc tcagaagtgt     540
atcaaagtac ggagatttta cattgcttag ggccagataa tcaagaaagt actgttcagc     600
caatgattac ttcaattcct cttaatctgt ggggtcgaga tttattacaa caatggggtg     660
cggaaatcac catgcccgct ccatcatata gccccacgag tcaaaaaatc atgaccaaga     720
tgggatatat accaggaaag ggactaggga aaaatgaaga tggcattaaa attccagttg     780
aggctaaaat aaatcaagaa agagaaggaa tagggtatcc ttttagggg cggccactgt      840 agagcctcct aaacccatac cattaacttg gaaaacagaa aaaccggtgt gggtaaatca     900
gtggccgcta ccaaaacaaa aactggaggc tttacattta ttagcgaatg aacagttaga     960
aaagggtcat attgagcctt cattctcacc ttggaattct cctgtgtttg taattcagaa    1020
gaaatcaggc aaatggcgta tgttaactga cttaagggcc gtaaacgccg taattcaacc    1080
catggggcct ctccaacctg ggttgccctc tctggccatg atcccaaaag actggccttt    1140
aattataatt gatctaaagg attgcttttt taccatccct ctggcggagc aggattgcga    1200
aaaatttgcc tttactatac cagc                                           1224

<210> SEQ ID NO 6
<211> LENGTH: 23
<212> TYPE: DNA
<213> ORGANISM: Artificial
<220> FEATURE:
<223> OTHER INFORMATION: Artifical primer

<400> SEQUENCE: 6
ccactgtaga gcctcctaaa ccc                                              23

<210> SEQ ID NO 7
<211> LENGTH: 26
<212> TYPE: DNA
<213> ORGANISM: Artificial
<220> FEATURE:
<223> OTHER INFORMATION: Synthetic primer

<400> SEQUENCE: 7
gctggtatag taaaggcaaa tttttc                                           26

<210> SEQ ID NO 8
<211> LENGTH: 250
<212> TYPE: DNA
<213> ORGANISM: Artificial
<220> FEATURE:
<223> OTHER INFORMATION: Synthetic primer

<400> SEQUENCE: 8
ccactgtaga gcctcctaaa cccataccat taacttggaa aacagaaaaa ccggtgtggg      60
taaatcagtg gccgctacca aaacaaaaac tggaggcttt acatttatta gcaaatgaac     120
agttagaaaa gggtcatatt gagccttcgt tctcaccttg gaattctcct gtgtttgtaa     180
ttcagaagaa atcaggcaaa tggcatatgt taactgactt aaaggccgta aacgccgtaa     240
ttcaacccat                                                            250
```

```
<210> SEQ ID NO 9
<211> LENGTH: 15
<212> TYPE: PRT
<213> ORGANISM: Artificial
<220> FEATURE:
<223> OTHER INFORMATION: Synthetic peptide

<400> SEQUENCE: 9

Leu Met Gln Asn Glu Ala Ile Glu Gln Val Arg Ala Ile Cys Leu
1               5                   10                  15

<210> SEQ ID NO 10
<211> LENGTH: 15
<212> TYPE: PRT
<213> ORGANISM: Artificial
<220> FEATURE:
<223> OTHER INFORMATION: Synthetic peptide

<400> SEQUENCE: 10

Ile Pro Tyr Asp Trp Glu Ile Leu Ala Lys Ser Ser Leu Ser Pro
1               5                   10                  15

<210> SEQ ID NO 11
<211> LENGTH: 15
<212> TYPE: PRT
<213> ORGANISM: Artificial
<220> FEATURE:
<223> OTHER INFORMATION: Synthetic peptide

<400> SEQUENCE: 11

Ala Asp Gln Leu Leu Gly Ile Gly Gln Asn Trp Ser Thr Ile Ser
1               5                   10                  15

<210> SEQ ID NO 12
<211> LENGTH: 15
<212> TYPE: PRT
<213> ORGANISM: Artificial
<220> FEATURE:
<223> OTHER INFORMATION: Synthetic peptide

<400> SEQUENCE: 12

Thr Ile Ser Gln Gln Ala Leu Met Gln Asn Glu Ala Ile Glu Gln
1               5                   10                  15

<210> SEQ ID NO 13
<211> LENGTH: 15
<212> TYPE: PRT
<213> ORGANISM: Artificial
<220> FEATURE:
<223> OTHER INFORMATION: Synthetic peptide

<400> SEQUENCE: 13

Glu Lys Ala Arg Lys Val Ile Val Glu Leu Met Ala Tyr Glu Asn
1               5                   10                  15

<210> SEQ ID NO 14
<211> LENGTH: 15
<212> TYPE: PRT
<213> ORGANISM: Artificial
<220> FEATURE:
<223> OTHER INFORMATION: Synthetic peptide

<400> SEQUENCE: 14

Met Ala Tyr Glu Asn Ala Asn Pro Glu Cys Gln Ser Ala Ile Lys
1               5                   10                  15

<210> SEQ ID NO 15
```

```
<211> LENGTH: 15
<212> TYPE: PRT
<213> ORGANISM: Artificial
<220> FEATURE:
<223> OTHER INFORMATION: Synthetic peptide

<400> SEQUENCE: 15

Pro Val Leu Asn Lys Gln Asn Ile Thr Ile Gln Ala Thr Thr Thr
1               5                   10                  15

<210> SEQ ID NO 16
<211> LENGTH: 15
<212> TYPE: PRT
<213> ORGANISM: Artificial
<220> FEATURE:
<223> OTHER INFORMATION: Synthetic peptide

<400> SEQUENCE: 16

Arg Ser Lys Phe Asp Lys Asn Gly Gln Pro Leu Ser Gly Asn Glu
1               5                   10                  15

<210> SEQ ID NO 17
<211> LENGTH: 15
<212> TYPE: PRT
<213> ORGANISM: Artificial
<220> FEATURE:
<223> OTHER INFORMATION: Synthetic peptide

<400> SEQUENCE: 17

Leu Ser Gly Asn Glu Gln Arg Gly Gln Pro Gln Ala Pro Gln Gln
1               5                   10                  15

<210> SEQ ID NO 18
<211> LENGTH: 15
<212> TYPE: PRT
<213> ORGANISM: Artificial
<220> FEATURE:
<223> OTHER INFORMATION: Synthetic peptide

<400> SEQUENCE: 18

Gln Pro Pro Leu Ser Gln Val Phe Gln Gly Ile Ser Gln Leu Pro
1               5                   10                  15

<210> SEQ ID NO 19
<211> LENGTH: 15
<212> TYPE: PRT
<213> ORGANISM: Artificial
<220> FEATURE:
<223> OTHER INFORMATION: Synthetic peptide

<400> SEQUENCE: 19

Glu Ile Ile Asp Lys Ser Arg Lys Glu Gly Asp Thr Glu Ala Trp
1               5                   10                  15

<210> SEQ ID NO 20
<211> LENGTH: 9
<212> TYPE: PRT
<213> ORGANISM: Artificial
<220> FEATURE:
<223> OTHER INFORMATION: Synthetic peptide

<400> SEQUENCE: 20

Val Ser Thr Lys Asn Leu Ile Lys Leu
1               5

<210> SEQ ID NO 21
<211> LENGTH: 9
<212> TYPE: PRT
```

```
<213> ORGANISM: Artificial
<220> FEATURE:
<223> OTHER INFORMATION: Synthetic peptide

<400> SEQUENCE: 21

Gly Ile Gly Gln Asn Trp Ser Thr Ile
1               5

<210> SEQ ID NO 22
<211> LENGTH: 9
<212> TYPE: PRT
<213> ORGANISM: Artificial
<220> FEATURE:
<223> OTHER INFORMATION: Synthetic peptide

<400> SEQUENCE: 22

Gln Tyr Gly Pro Asn Ser Pro Tyr Met
1               5

<210> SEQ ID NO 23
<211> LENGTH: 9
<212> TYPE: PRT
<213> ORGANISM: Artificial
<220> FEATURE:
<223> OTHER INFORMATION: Synthetic peptide

<400> SEQUENCE: 23

Cys Pro Val Leu Asn Lys Gln Asn Ile
1               5

<210> SEQ ID NO 24
<211> LENGTH: 9
<212> TYPE: PRT
<213> ORGANISM: Artificial
<220> FEATURE:
<223> OTHER INFORMATION: Synthetic peptide

<400> SEQUENCE: 24

Leu Thr Val Trp Asn Asp Trp Ala Ile
1               5

<210> SEQ ID NO 25
<211> LENGTH: 9
<212> TYPE: PRT
<213> ORGANISM: Artificial
<220> FEATURE:
<223> OTHER INFORMATION: Synthetic peptide

<400> SEQUENCE: 25

Lys Phe Asp Lys Asn Gly Gln Pro Leu
1               5

<210> SEQ ID NO 26
<211> LENGTH: 9
<212> TYPE: PRT
<213> ORGANISM: Artificial
<220> FEATURE:
<223> OTHER INFORMATION: Synthetic peptide

<400> SEQUENCE: 26

Gly Lys Cys Tyr Asn Cys Gly Gln Ile
1               5

<210> SEQ ID NO 27
<211> LENGTH: 9
<212> TYPE: PRT
<213> ORGANISM: Artificial
<220> FEATURE:
```

<223> OTHER INFORMATION: Synthetic peptide

<400> SEQUENCE: 27

His Leu Lys Lys Asn Cys Pro Val Leu
1               5

<210> SEQ ID NO 28
<211> LENGTH: 9
<212> TYPE: PRT
<213> ORGANISM: Artificial
<220> FEATURE:
<223> OTHER INFORMATION: Synthetic peptide

<400> SEQUENCE: 28

Gly Arg Lys Gly Asn Ile Ile Pro Leu
1               5

<210> SEQ ID NO 29
<211> LENGTH: 9
<212> TYPE: PRT
<213> ORGANISM: Artificial
<220> FEATURE:
<223> OTHER INFORMATION: Synthetic peptide

<400> SEQUENCE: 29

Phe Ser Ile Lys Met Leu Lys Asp Met
1               5

<210> SEQ ID NO 30
<211> LENGTH: 15
<212> TYPE: PRT
<213> ORGANISM: Artificial
<220> FEATURE:
<223> OTHER INFORMATION: Synthetic peptide

<400> SEQUENCE: 30

Pro Ala Val Asp Ser Asp Leu Thr Glu Ser Leu Asp Lys His Lys
1               5                   10                  15

<210> SEQ ID NO 31
<211> LENGTH: 15
<212> TYPE: PRT
<213> ORGANISM: Artificial
<220> FEATURE:
<223> OTHER INFORMATION: Synthetic peptide

<400> SEQUENCE: 31

Trp Asn Ser Gln Ser Ser Ile Asp Gln Lys Leu Ala Asn Gln Ile
1               5                   10                  15

<210> SEQ ID NO 32
<211> LENGTH: 15
<212> TYPE: PRT
<213> ORGANISM: Artificial
<220> FEATURE:
<223> OTHER INFORMATION: Synthetic peptide

<400> SEQUENCE: 32

Val Ser Met Asp Arg Pro Trp Glu Ala Ser Pro Ser Val His Ile
1               5                   10                  15

<210> SEQ ID NO 33
<211> LENGTH: 15
<212> TYPE: PRT
<213> ORGANISM: Artificial
<220> FEATURE:
<223> OTHER INFORMATION: Synthetic peptide

```
<400> SEQUENCE: 33

Pro Ala Val Gln Asn Trp Leu Val Glu Val Pro Thr Val Ser Pro
1               5                   10                  15

<210> SEQ ID NO 34
<211> LENGTH: 15
<212> TYPE: PRT
<213> ORGANISM: Artificial
<220> FEATURE:
<223> OTHER INFORMATION: Synthetic peptide

<400> SEQUENCE: 34

Leu Arg Pro Arg Val Asn Tyr Leu Gln Asp Phe Ser Tyr Gln Arg
1               5                   10                  15

<210> SEQ ID NO 35
<211> LENGTH: 15
<212> TYPE: PRT
<213> ORGANISM: Artificial
<220> FEATURE:
<223> OTHER INFORMATION: Synthetic peptide

<400> SEQUENCE: 35

Asn Thr Glu Val Leu Val Trp Glu Glu Cys Val Ala Asn Ser Ala
1               5                   10                  15

<210> SEQ ID NO 36
<211> LENGTH: 15
<212> TYPE: PRT
<213> ORGANISM: Artificial
<220> FEATURE:
<223> OTHER INFORMATION: Synthetic peptide

<400> SEQUENCE: 36

Ser Ala Val Ile Leu Gln Asn Asn Glu Phe Gly Thr Ile Ile Asp
1               5                   10                  15

<210> SEQ ID NO 37
<211> LENGTH: 15
<212> TYPE: PRT
<213> ORGANISM: Artificial
<220> FEATURE:
<223> OTHER INFORMATION: Synthetic peptide

<400> SEQUENCE: 37

Gln Phe Tyr His Asn Cys Ser Gly Gln Thr Gln Ser Cys Pro Ser
1               5                   10                  15

<210> SEQ ID NO 38
<211> LENGTH: 15
<212> TYPE: PRT
<213> ORGANISM: Artificial
<220> FEATURE:
<223> OTHER INFORMATION: Synthetic peptide

<400> SEQUENCE: 38

Asn Arg Ser Lys Arg Phe Ile Phe Thr Leu Ile Ala Val Ile Met
1               5                   10                  15

<210> SEQ ID NO 39
<211> LENGTH: 9
<212> TYPE: PRT
<213> ORGANISM: Artificial
<220> FEATURE:
<223> OTHER INFORMATION: Synthetic peptide

<400> SEQUENCE: 39
```

```
Pro Tyr Met Leu Val Val Gly Asn Ile
1               5

<210> SEQ ID NO 40
<211> LENGTH: 9
<212> TYPE: PRT
<213> ORGANISM: Artificial
<220> FEATURE:
<223> OTHER INFORMATION: Synthetic peptide

<400> SEQUENCE: 40

Ile Phe Lys Ala Ser Lys Ala His Leu
1               5

<210> SEQ ID NO 41
<211> LENGTH: 9
<212> TYPE: PRT
<213> ORGANISM: Artificial
<220> FEATURE:
<223> OTHER INFORMATION: Synthetic peptide

<400> SEQUENCE: 41

Lys Thr Ile Gly Ser Thr Thr Ile Ile
1               5

<210> SEQ ID NO 42
<211> LENGTH: 9
<212> TYPE: PRT
<213> ORGANISM: Artificial
<220> FEATURE:
<223> OTHER INFORMATION: Synthetic peptide

<400> SEQUENCE: 42

Gly Tyr His Tyr Pro Pro Ile Cys Leu
1               5

<210> SEQ ID NO 43
<211> LENGTH: 9
<212> TYPE: PRT
<213> ORGANISM: Artificial
<220> FEATURE:
<223> OTHER INFORMATION: Synthetic peptide

<400> SEQUENCE: 43

Ser Tyr Gln Arg Ser Leu Lys Phe Arg
1               5

<210> SEQ ID NO 44
<211> LENGTH: 9
<212> TYPE: PRT
<213> ORGANISM: Artificial
<220> FEATURE:
<223> OTHER INFORMATION: Synthetic peptide

<400> SEQUENCE: 44

Lys Gly Lys Pro Cys Pro Lys Glu Ile
1               5

<210> SEQ ID NO 45
<211> LENGTH: 9
<212> TYPE: PRT
<213> ORGANISM: Artificial
<220> FEATURE:
<223> OTHER INFORMATION: Synthetic peptide

<400> SEQUENCE: 45

Val Glu Val Pro Thr Val Ser Pro Ile
1               5
```

<210> SEQ ID NO 46
<211> LENGTH: 9
<212> TYPE: PRT
<213> ORGANISM: Artificial
<220> FEATURE:
<223> OTHER INFORMATION: Synthetic peptide

<400> SEQUENCE: 46

Ser Leu Arg Pro Arg Val Asn Tyr Leu
1               5

<210> SEQ ID NO 47
<211> LENGTH: 9
<212> TYPE: PRT
<213> ORGANISM: Artificial
<220> FEATURE:
<223> OTHER INFORMATION: Synthetic peptide

<400> SEQUENCE: 47

Thr Phe Asn Trp Gln His Arg Ile Leu
1               5

<210> SEQ ID NO 48
<211> LENGTH: 170
<212> TYPE: DNA
<213> ORGANISM: Human endogenous retrovirus

<400> SEQUENCE: 48
cacacaggaa acagctatga ccatgattac gccaagctca gaattaaccc tcactaaagg        60
gactagtcct gcaggtttaa acgaattcgc ccttaagggc gaattcgcgg ccgctaaatt       120
caattcgccc tatagtgagt cgtattacaa ttcactggcc gtcgttttac                  170

<210> SEQ ID NO 49
<211> LENGTH: 170
<212> TYPE: DNA
<213> ORGANISM: Human endogenous retrovirus

<400> SEQUENCE: 49
gtgtgtcctt tgtcgatact ggtactaatg cggttcgagt cttaattggg agtgatttcc        60
ctgatcagga cgtccaaatt tgcttaagcg gaattcccg cttaagcgcc ggcgatttaa        120
gttaagcggg atatcactca gcataatgtt aagtgaccgg cagcaaaatg                  170

<210> SEQ ID NO 50
<211> LENGTH: 156
<212> TYPE: DNA
<213> ORGANISM: Artificial
<220> FEATURE:
<223> OTHER INFORMATION: Synthetic primer

<400> SEQUENCE: 50
ttaaacgaat tcgcccttgc tagggtgata atggggcaaa ctaaagtaa aattaaaagt         60 aaatatgcct cttatctcaa gccagttacc acaatacaac aattgtcccc caccacaagc       120
ggcagtgcag cagtagaagg gcgaatcgcg gccgct                                 156

<210> SEQ ID NO 51
<211> LENGTH: 156
<212> TYPE: DNA
<213> ORGANISM: Artificial
<220> FEATURE:
<223> OTHER INFORMATION: Synthetic primer

<400> SEQUENCE: 51

```
ttaaacgaat tcgcccttca agcggcagtg cagcagtaga tttatgtact atacaagcag    60
tctctctgct tccaggggtt tttaccatcc ctctggcgga gcaggattgc gaaaaatttg   120
cctttactat acaagcaagg gcgaatcgcg gccgct                             156
```

```
<210> SEQ ID NO 52
<211> LENGTH: 156
<212> TYPE: DNA
<213> ORGANISM: Artificial
<220> FEATURE:
<223> OTHER INFORMATION: Synthetic primer

<400> SEQUENCE: 52
ttaaacgaat tcgcccttga aaaatttgcc tttactatac cagccataaa taataaagaa    60
ccagccacca ggtttcagct tcctgtttgg atacccacta gacatttgaa gttctacaat   120
gaacccatca gagagcaagg gcgaatcgcg gccgct                             156
```

```
<210> SEQ ID NO 53
<211> LENGTH: 156
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (70)..(70)
<223> OTHER INFORMATION: n is a, c, g, or t

<400> SEQUENCE: 53
ttaaacgaat tcgcccttct acatgaaccc atcagagatg caaagaaaag cacctccgcg    60
gagacggagn acaccgcaca agagagatca gattgtcact gtgtctgtgt agaaagaagt   120
agacatagga gactccaagg gcgaatcgcg gccgct                             156
```

```
<210> SEQ ID NO 54
<211> LENGTH: 24
<212> TYPE: DNA
<213> ORGANISM: Artificial
<220> FEATURE:
<223> OTHER INFORMATION: Synthetic primer

<400> SEQUENCE: 54
cacaggtcaa accgcctagg aatg                                           24
```

```
<210> SEQ ID NO 55
<211> LENGTH: 22
<212> TYPE: DNA
<213> ORGANISM: Artificial
<220> FEATURE:
<223> OTHER INFORMATION: Synthetic primer

<400> SEQUENCE: 55
tcctgctcaa cttcctgtcg ag                                             22
```

```
<210> SEQ ID NO 56
<211> LENGTH: 26
<212> TYPE: DNA
<213> ORGANISM: Artificial
<220> FEATURE:
<223> OTHER INFORMATION: Synthetic primer

<400> SEQUENCE: 56
tctttagcga gacgctacca tggcta                                         26
```

-continued

```
<210> SEQ ID NO 57
<211> LENGTH: 27
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (25)..(25)
<223> OTHER INFORMATION: n = t and/or c

<400> SEQUENCE: 57
cattccttgt ggtaaaactt tccantg                                27

<210> SEQ ID NO 58
<211> LENGTH: 25
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (23)..(23)
<223> OTHER INFORMATION: n is a, c, g, or t

<400> SEQUENCE: 58 cccctttggaa tactcctgtt ttntg                                 25

<210> SEQ ID NO 59
<211> LENGTH: 81
<212> TYPE: PRT
<213> ORGANISM: Artificial
<220> FEATURE:
<223> OTHER INFORMATION: Synthetic peptide

<400> SEQUENCE: 59

Ile Lys Lys Lys Ser Gly Lys Trp Arg Met Leu Thr Asp Leu Arg Ala
 1               5                  10                  15

Ile Asn Ser Val Ile Gln Pro Met Gly Ala Leu Gln Pro Gly Leu Pro
             20                  25                  30

Ser Pro Ala Ile Ile Pro Lys Asn Trp Pro Leu Val Val Ile Asp Leu
         35                  40                  45

Lys Asp Ser Phe Phe Thr Ile Pro Leu Ala Asp Gln Asp Cys Glu Trp
     50                  55                  60

Phe Ala Phe Ile Ile Pro Ala Val Asn Asn Leu Gln Pro Ala Lys His
 65                  70                  75                  80

Phe
```